(12) United States Patent
Yang et al.

(10) Patent No.: US 12,268,761 B2
(45) Date of Patent: Apr. 8, 2025

(54) METHOD OF MASKING A DENTAL SUPPORT STRUCTURE OF A DENTAL PROSTHESIS MADE OF HIGHLY TRANSLUCENT CERAMIC MATERIAL

(71) Applicant: James R. Glidewell Dental Ceramics, Inc., Newport Beach, CA (US)

(72) Inventors: Yan Yang, Irvine, CA (US); Sreeram Balasubramanian, Irvine, CA (US); Yang Soon Park, Aliso Viejo, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 18/655,570

(22) Filed: May 6, 2024

(65) Prior Publication Data

US 2024/0285479 A1    Aug. 29, 2024

Related U.S. Application Data

(62) Division of application No. 17/166,942, filed on Feb. 3, 2021, now Pat. No. 12,005,131.

(60) Provisional application No. 62/969,236, filed on Feb. 3, 2020.

(51) Int. Cl.
| | |
|---|---|
| *A61K 6/80* | (2020.01) |
| *A61K 6/15* | (2020.01) |
| *A61K 6/818* | (2020.01) |
| *A61K 6/84* | (2020.01) |
| *C04B 35/48* | (2006.01) |
| *C04B 35/63* | (2006.01) |

(52) U.S. Cl.
CPC ............ *A61K 6/818* (2020.01); *A61K 6/15* (2020.01); *A61K 6/84* (2020.01); *C04B 35/48* (2013.01); *C04B 35/6303* (2013.01); *C04B 2235/3246* (2013.01); *C04B 2235/9661* (2013.01)

(58) Field of Classification Search
CPC ....................................................... A61K 6/80
See application file for complete search history.

(56) References Cited

U.S. PATENT DOCUMENTS

| | | | |
|---|---|---|---|
| 8,697,176 B2 * | 4/2014 | Wang | A61K 6/818 |
| | | | 427/372.2 |
| 9,095,403 B2 * | 8/2015 | Carden | A61K 6/804 |
| 9,365,459 B2 | 6/2016 | Carden et al. | |
| 9,434,651 B2 | 9/2016 | Carden et al. | |
| (Continued) | | | |

OTHER PUBLICATIONS

Oh et al., "Effect of abutment shade, ceramic thickness, and coping type on the final shade of zirconia all-ceramic restorations: in vitro study of color masking ability," *J. Adv. Prosthodont.*, 2015, 7: 368-374 (2015).

*Primary Examiner* — Cachet I Proctor
(74) *Attorney, Agent, or Firm* — Klarquist Sparkman, LLP

(57) ABSTRACT

A method for masking the appearance of a support structure underlying a highly translucent ceramic dental restoration is provided. The porous form of a zirconia ceramic dental restoration is treated with a liquid masking composition comprising 0.4 wt % to 50 wt % of one or more masking agents. The masking composition is applied to the internal surface of a restoration and a region of the facial surface of the restoration that is opposite the internal surface. After application of the masking compositions, treated zirconia restoration is sintered to greater than 98% theoretical density.

7 Claims, 8 Drawing Sheets

(56) References Cited

U.S. PATENT DOCUMENTS

| | | | |
|---|---|---|---|
| 9,512,317 B2 | 12/2016 | Carden et al. | |
| 9,790,129 B2 | 10/2017 | Carden et al. | |
| 9,822,039 B1* | 11/2017 | Xu | C08K 3/22 |
| 9,872,746 B2* | 1/2018 | Hauptmann | A61C 5/77 |
| 10,292,795 B2* | 5/2019 | Herrmann | C09D 133/066 |
| 11,534,276 B2* | 12/2022 | Meyer | A61C 13/0004 |
| 2004/0081767 A1* | 4/2004 | Pfaendtner | C23C 8/04 |
| | | | 427/248.1 |
| 2007/0077534 A1* | 4/2007 | Saliger | B22F 3/1125 |
| | | | 433/167 |
| 2016/0331494 A1* | 11/2016 | Morales | A61C 13/08 |
| 2017/0189143 A1* | 7/2017 | Wolz | A61C 13/0022 |
| 2018/0002235 A1* | 1/2018 | Ito | A61C 8/0012 |
| 2018/0235847 A1 | 8/2018 | Balasubramanian et al. | |
| 2018/0263863 A1* | 9/2018 | Kim | A61K 6/822 |
| 2018/0265420 A1* | 9/2018 | Kim | A61K 6/78 |
| 2019/0127284 A1 | 5/2019 | Balasubramanian et al. | |
| 2019/0284103 A1* | 9/2019 | Cornell | C04B 41/009 |
| 2019/0388196 A1* | 12/2019 | Kitamura | C04B 41/5007 |

\* cited by examiner

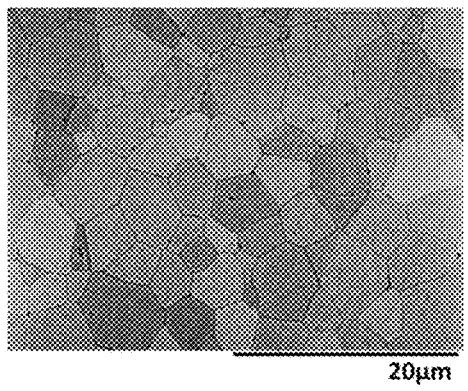
FIG. 3A – Zinc 10%
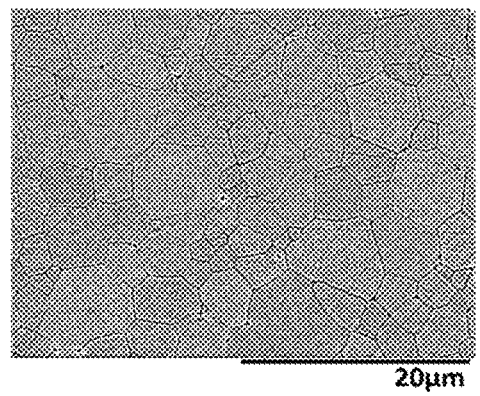
FIG. 4A – Aluminum Chloride 10%
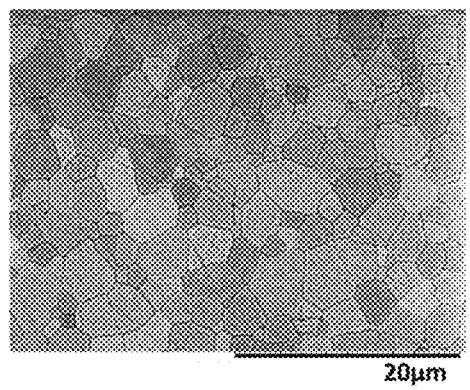
FIG. 3B – Zinc 20%
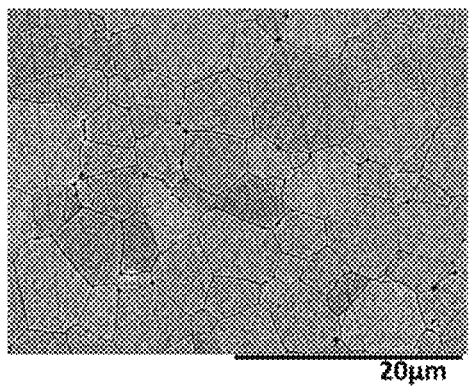
FIG. 4B – Aluminum Chloride 20%
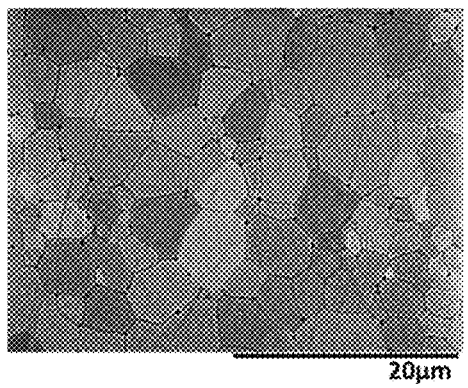
FIG. 3C – Zinc 30%
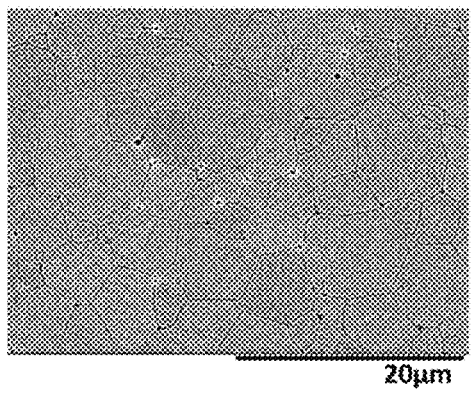
FIG. 4C – Aluminum Chloride 30%

900

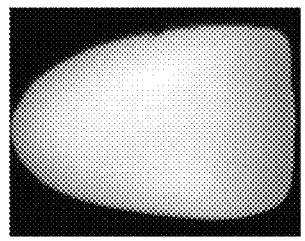 Ex. 66
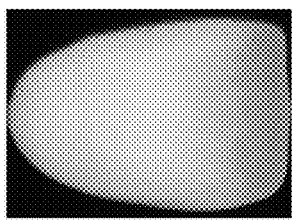 Ex. 67
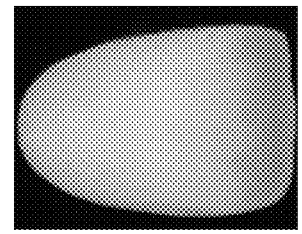 Ex. 68
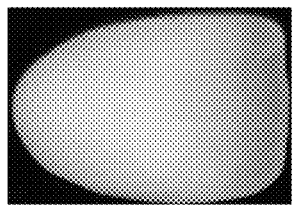 Ex. 69
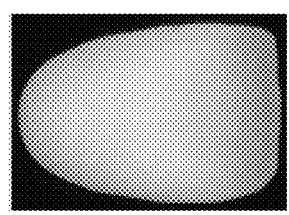 Ex. 70
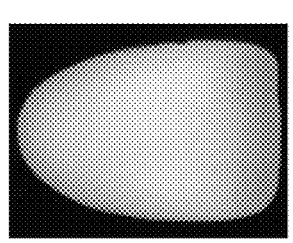 Ex. 71
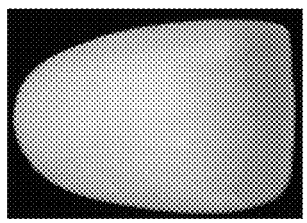 Ex. 72
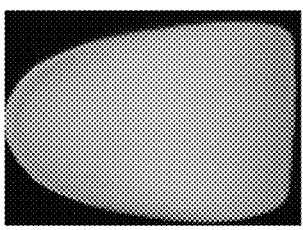 Ex. 73
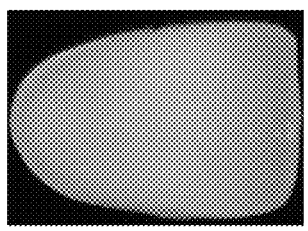 Ex. 74
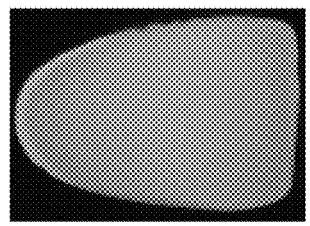 Ex. 75
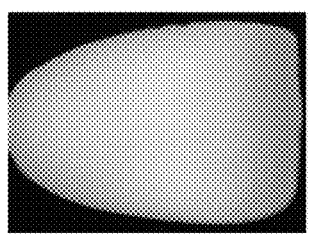 Ex. 76
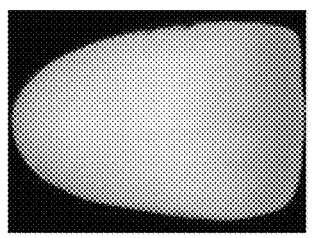 Ex. 77
FIG. 11

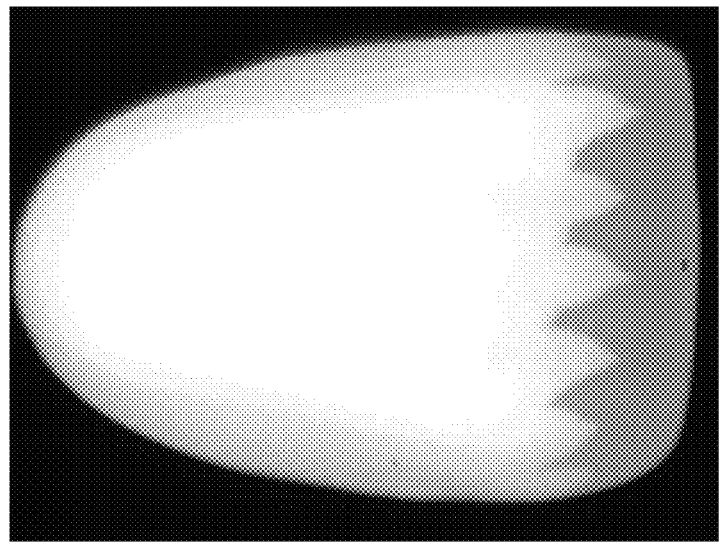
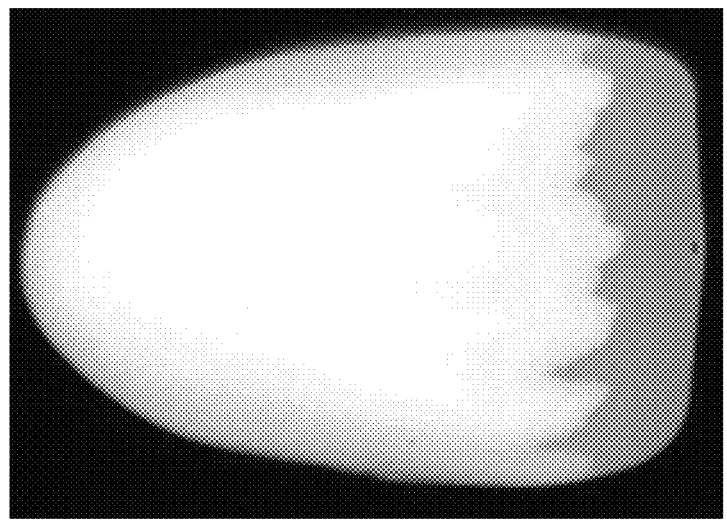
Fig. 12

METHOD OF MASKING A DENTAL SUPPORT STRUCTURE OF A DENTAL PROSTHESIS MADE OF HIGHLY TRANSLUCENT CERAMIC MATERIAL

RELATED APPLICATIONS

This application is a divisional of and claims the benefit of and priority to U.S. patent application Ser. No. 17/166,942, filed Feb. 3, 2021, which claims the benefit of and priority to U.S. Provisional Patent Application No. 62/969,236, filed Feb. 3, 2020. The entireties of each of the foregoing applications are incorporated herein by reference.

BACKGROUND

Yttria-stabilized zirconia is known for use in making dental prostheses such as veneers, crowns, bridges or dentures because of its good mechanical properties. Advantageously, yttria-stabilized zirconia also has enhanced translucency in sintered materials when stabilized with about 4 mol % yttria or higher. However, where a patient's underlying tooth preparation is a dark shade, it may be visible through the facial surface of a highly translucent dental prosthesis. Similarly, a dental implant or implant abutment to which an implant-supported prosthesis is connected may also be visible through highly translucent zirconia dental prosthesis materials.

While a support structure (for example, a tooth preparation or implant) may be less visible beneath a dental prosthetic made from zirconia stabilized with lower concentrations of yttria, the prosthesis may lack the translucency of natural dentition. Moreover, a dental prosthesis milled from a zirconia ceramic block having a uniform concentration of yttria throughout the block may lack a translucency gradient inherent in natural dentition. For example, in natural anterior dentition, translucency is highest at the incisal edge, gradually decreasing towards the gingival margin. To achieve a translucency gradient, a dental prosthesis may be made from a layered zirconia ceramic block having varying concentrations of yttria in each layer; however, the prosthesis may have shrinkage-related distortion during sintering due to coefficient of thermal expansion (CTE) mismatching between layers.

In U.S. Pat. Pub. 2018/0002235 A1, multilayered blocks having laminated or stacked layers of differing ΔL* values are disclosed. A light shielding material, e.g., silicon oxide, aluminum oxide, titanium oxide, or a complex oxide of zirconium and silicon, is added to partially stabilized zirconia. The variation in ΔL values between adjacent layers is achieved where a first layer, formed from a first zirconia powder to which a lower content of light shielding material is added, is adjacent a second layer, formed from a second zirconia powder having a higher content of light shielding material. A dental prosthesis made from the layered block comprises the first layer on the incisal side and the second layer on the cervical side, covering the side surface of an abutment tooth.

SUMMARY

A method is provided herein for masking the visibility of a dental support structure, underlying a highly translucent dental prosthesis by the application of a masking agent to the prosthesis. Support structures that are visible through highly translucent prostheses may include dental implant abutments, denture bars, a patient's natural tooth or the remaining portion of a patient's natural tooth (tooth preparation) that has been reduced for attachment to a prosthesis.

Masking agents may be applied to reduce the translucency of highly translucent, sintered dental prostheses made from yttria-stabilized zirconia ceramic materials comprising 4 mol % yttria or higher, such as 4.5 mol % to 7 mol %. Highly translucent yttria-stabilized zirconia materials used for making prostheses described herein may have a transmittance between 45% and 80% at 700 nm when measured on a 1 mm thick sintered body. Thin zirconia prostheses having lower transmittance measurements (e.g., about 35% to 45% at 700 nm on a 1 mm thick, sintered ceramic body), such as yttria-stabilized zirconia ceramic materials comprising 3 mol % yttria to 4 mol % yttria, may also be treated by methods described herein to block the visibility of an underlying substructure. Examples of thin prostheses include veneers having a thickness between 0.1 mm and 1.0 mm. Zirconia ceramic dental prostheses suitable for use herein also include but are not limited to crowns, single or multi-unit bridges, and implant-supported partial or full-arch dentures. Treated regions of zirconia ceramic bodies provided herein may have a reduction in transmittance of at least 3%, such as at least 5%, such as at least 7%, such as at least 10% (when measured at 700 nm on 1 mm thick sintered body) compared to an untreated body made from the same material. Treated ceramic bodies may further have an opacity between 40% to 70%, when measured by the methods provided herein.

To mask the visibility of a dental support structure through a dental prosthesis, the translucency (measured as percent transmittance) of the dental prosthesis may be selectively decreased on a facial surface that is in front of the support structure when installed in the mouth of a patient. Additionally, an internal, or fitting, surface of a dental prosthesis that has been shaped for attachment to the support structure may be treated with a masking mixture. Visibility of an underlying support structure through the zirconia prosthesis may be influenced by factors such as color, size and location of the underlying support structure, as well as the translucency, thickness, color and/or shade of the final prosthesis in areas adjacent the support structure.

In one embodiment, a masking mixture is applied to the internal surface to mask an underlying support structure. In another embodiment, the masking mixture is applied to a region of the facial surface that is opposite the internal surface, rather than applying the masking mixture to the internal surface directly. In some embodiments, the masking agent that is applied to internal surfaces becomes visible through the prosthesis. For example, a treated internal surface may create a distinct horizontal boundary having lower translucency where masking mixture accumulates on an internal bottom surface that is visible across the facial surface of the prosthesis. In this embodiment, a portion of the facial surface of the dental prosthesis that is opposite the treated internal bottom surface also may be treated with a masking mixture. The masking mixture used to treat the internal surface and the facial surface opposite the internal surface may comprise the same or different masking agent.

DESCRIPTION OF THE DRAWINGS

FIGS. 3A, 3B and 3C are SEM images of three exemplary embodiments.

FIGS. 4A, 4B and 4C are SEM images of three exemplary embodiments.

FIG. 11 includes spectral images of crowns corresponding to Examples 66 through 77 described herein.

FIG. 12 includes spectral images of crowns corresponding to Comparative Examples CE2 and CE3 described herein.

DETAILED DESCRIPTION

Figure 1A:
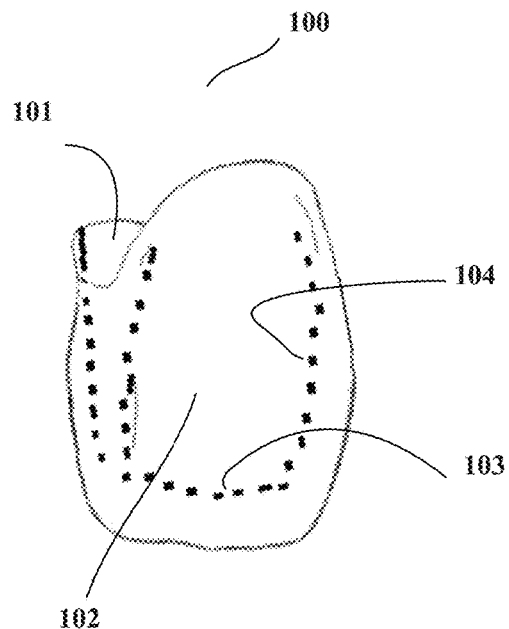
FIG. 1A is a front perspective view of an illustration of an exemplary dental prosthesis.

A method is provided herein for masking the visibility of an underlying dental support structure through a dental prosthesis that is made of highly translucent yttria-stabilized zirconia. A liquid masking mixture, a method of selectively applying the masking mixture to a porous dental prosthesis prior to sintering, and a sintered, highly translucent dental prosthesis comprising a masking agent, are also provided. Dental prostheses may be in the form of a crown, veneer, single or multi-unit bridge, implant-supported partial or full-arch denture, and the like, that attach to the support structure of a patient, such as an implant abutment or natural tooth preparation.

A liquid masking mixture comprises a solvent and one or more masking agents that can penetrate the porosity of a porous ceramic body in an amount effective for reducing the visibility an underlying support structure through the sintered form of the porous dental prosthesis to which the masking mixture is applied. The liquid masking mixture may be, for example, a solution, suspension or colloid.

A masking agent comprises a metal-containing component, such as a metal complex or metallic compound, for example, a metallic salt. Metal-containing components suitable for use as masking agents comprise oxides or salts of one or more elements selected from Zn, Ti, La, Al, Ca, Mn, Mg, Si, Sc and Sr, or a combination thereof. Metal-containing components may comprise an anion such as acetate, oxalate, sulfate, carbonate, chloride, nitrate, phosphate or citrate.

Examples of masking agents include, but are not limited to, aluminum chloride (e.g., $AlCl_3 \cdot 6H_2O$), zinc sulfate (e.g., $ZnSO_4 \cdot 7H_2O$), zinc nitrate (e.g., $Zn(NO_3)_2 \cdot 6H_2O$), scandium chloride (e.g., $ScCl_3 \cdot 6H_2O$), magnesium nitrate (e.g., $Mg(NO_3)_2 \cdot 6H_2O$), lanthanum nitrate (e.g., $La(NO_3)_3 \cdot 6H_2O$), titanium butoxide ($Ti[O(CH_2)_3CH_3]_4$), potassium silicate (e.g., $K_2SiO_3$), tetrasodium pyrophosphate (e.g., $Na_4P_2O_7 \cdot 10H_2O$), calcium nitrate (e.g., $Ca(NO_3)_2 \cdot 4H_2O$, and strontium nitrate (e.g., $Sr(NO_3)_2$). The masking agents may be used alone, or two or more may be combined to form a masking mixture.

The liquid component of the masking mixture may be aqueous or non-aqueous, including but not limited to water, inorganic solvents, such as water, organic solvents such as ethanol alcohol, isopropyl alcohol, and combinations thereof. The liquid masking mixture may comprise from 0.4 wt % to 50 wt % of the masking agent, based on the total weight of the liquid masking mixture, or from 5 wt % to 40 wt %, or from 8 wt % to 30 wt %, or from 10 wt % to 30 wt %, or from 20 wt % to 30 wt %, of the masking agent based on the total weight of the liquid masking composition. In one embodiment, a liquid masking mixture comprises from 0.4 wt % to 50 wt % of $AlCl_3 \cdot 6H_2O$, based on the total weight of the liquid masking mixture. In one embodiment, an aqueous liquid masking mixture comprises a combination of aluminum chloride and zinc sulfate. For example, an aqueous masking mixture comprises from 0.4 wt % to 40 wt % of $AlCl_3 \cdot 6H_2O$ and from 5 wt % to 40 wt % of $ZnSO_4 \cdot 7H_2O$, based on the total weight of the liquid masking mixture.

The liquid masking mixture may comprise from 5 g/L to 500 g/L of the metal ion of the masking agent, or from 5 g/L to 450 g/L, or from 5 g/L to 400 g/L, or from 5 g/L to 300 g/L, of the metal ion of the masking agent in the liquid masking mixture. In one embodiment, an aqueous masking mixture comprises from 5 g/L to 300 g/L of aluminum. In a further embodiment, an aqueous masking mixture comprises from 5 g/L to 300 g/L of aluminum and from 10 g/L to 200 g/L of zinc.

The liquid masking mixture may further comprise a coloring agent to create a dentally acceptable shade in the final sintered zirconia prosthesis. Coloring agents may include, but are not limited to metal-containing oxides, salts, or other compounds or complexes that include erbium (Er), terbium (Tb), chromium (Cr), cobalt (Co), iron (Fe), manganese (Mn), nickel (Ni), praseodymium (Pr), copper (Cu), and combinations thereof. Coloring agents disclosed in commonly owned US Patent Publication Nos. U.S. Pat. Nos. 9,095,403, 9,365,459, and 9,512,317, each of which is incorporated by reference herein in their entirety, may be suitable for use herein. Coloring agents may be added to the masking mixture to achieve a final color in the sintered yttria-stabilized zirconia ceramic material that matches a shade tab from a Vita A1-D4® Classical Shades shade guide or Vita Bleached Shades shade guide, such as 0M1, 0M2 or 0M3 bleach shades, (available through Vita North America) when measured according to the shade match evaluation test method provided herein.

In some embodiments, a coloring agent in the form of a metallic salt is selected that is soluble in an aqueous liquid masking mixture. The amount of coloring agent may be present in the range of approximately 0.001 wt % to approximately 60 wt % metallic salt based on the total weight of the liquid masking mixture. In some embodiments, the amount of metal agents as colorant in the liquid masking mixture may be from 0.0001 g/L to about 500 g/L, or 0.0001 g/L to about 400 g/L, 0.0001 g/L to about 300 g/L based on the coloring agent metal ion per liter of H2O.

In other embodiments, masking agents may be added to the coloring solution to form a masking mixture. One or more masking agents may be added to the coloring solution as a liquid or solid. In another embodiment, one or more masking agents and one or more coloring agents, in the form of metal-containing oxides, salts, or other compounds or complexes, may be combined to form a masking mixture when added to a liquid. Other esthetic additives may be added to masking mixtures to obtain desired opalescence or fluorescence properties for dental applications. A wetting agent, such as n-propanol, glycerol, ethylene glycol or polyethylene glycol (e.g., PEG 200 or PEG 400) may be added to the masking mixture in an amount of approximately 0.1 wt % to 5 wt %, based on the total weight of the masking mixture, to control the penetration depth of the masking agent in the porous ceramic body.

Liquid masking mixtures may be applied by techniques such as painting by brushing, or by dipping, or dripping, liquid masking mixtures onto the porous dental prosthesis. Liquid masking mixtures may be applied by known techniques for distributing liquid compositions onto ceramic surfaces, including coating with a marker or felt-tip pen that is loaded with the liquid mixture, or by use of a sponge.

Visibility of the support structure through the sintered prosthesis may be influenced by factors such as color, size and location of the underlying support structure, as well as translucency, thickness, color and/or shade of the final prosthesis in regions adjacent the support structure. In one method, a liquid masking mixture is applied to one or more surfaces of a porous highly translucent zirconia ceramic dental prosthesis to selectively reduce visibility of the underlying support structure. Highly translucent yttria-stabilized zirconia materials may include materials having between 45% and 80% transmittance at 700 nm when measured on a 1 mm thick sintered body. In another method, a masking mixture may be used for zirconia ceramic materials having lower transmittance measurements (e.g., about 35% to 45% at 700 nm on a 1 mm thick, sintered ceramic body) where the final prosthesis is very thin. For example, a liquid masking mixture may be applied to the attachment side of a veneer having a thickness between 0.1 mm and 1.0 mm. In some embodiments, treated regions of a zirconia ceramic body may have a reduction in percent transmittance of at least 5%, or at least 10%, or at least 15%, or between 5% and 25%, (when measured at 700 nm on a 1 mm thick sintered body), compared to an untreated ceramic body made from the same ceramic material. In other embodiments, the transmittance of a treated region of a ceramic body may be less than or equal to 60%, or less than or equal to 55%, or less than or equal to 50%, or less than or equal to 45%, (when measured at 700 nm on a 1 mm thick sintered body). Treated zirconia ceramic dental restorations may further comprise an opacity between 40% to 70%, when measured by the methods provided herein.

Figure 1B:
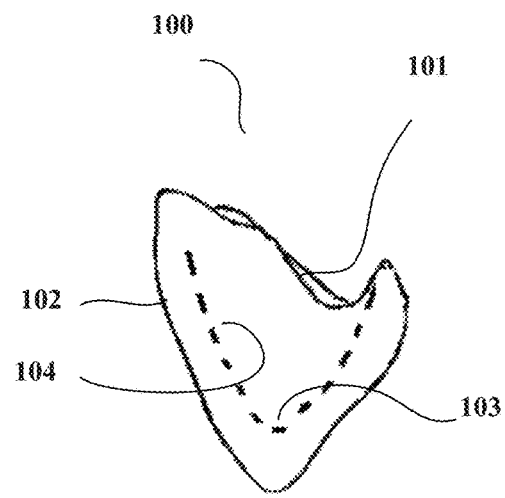
FIG. 1B is a side view of an illustration of an exemplary dental prosthesis.

An exemplary dental prosthesis is illustrated in FIGS. 1A and 1B, depicting a dental crown 100 comprises an internal space or cavity 101 (shown in dashed lines) that has been shaped to fit over a patient's support structure, such as a natural tooth, tooth preparation or implant abutment. In some embodiments, a liquid masking mixture may be applied to the exterior of the crown on a portion of the facial surface 102 that faces the lips or cheeks of a patient. In some embodiments, to retain the high translucency of the zirconia ceramic adjacent the incisal edge, the masking mixture is applied in a manner that avoids treating the incisal edge, for example, by brushing on the crown at a distance that is at least 0.1 mm to 5 mm away from the incisal edge.

In other embodiments, a liquid masking mixture may be applied to an internal surface (fitting surface) of the crown that fits over the support structure. The liquid masking mixture may be applied to the internal bottom surface 103 that may be adjacent the incisal region of the patient's tooth preparation upon installation. Alternatively, the liquid masking mixture may be applied to the internal side surfaces 104, of the prosthesis that may be adjacent the side surfaces of a tooth preparation. In some embodiments, the liquid masking mixture may be applied to both the internal bottom surface and the internal side surfaces of the prosthesis.

Figure 2:
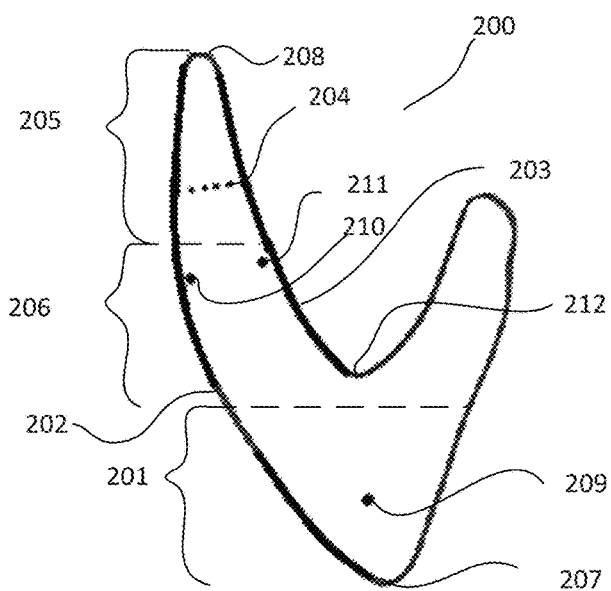
FIG. 2 is an illustration of a cross-section of an exemplary dental prosthesis analyzed by EDS according to one embodiment.

With reference to FIG. 2, a first masking mixture may be applied to the facial surface (202) of the crown that is opposite the internal side surface (203). In some embodiments, the first masking mixture is applied to approximately the top two-thirds (205, 206) of the facial surface when measured from the crown margin (208) at the facial surface towards the incisal edge (207). The first masking mixture may be applied to the facial surface (202) and the internal side surface (203), the internal bottom surface (212), or both. In some embodiments, the masking mixture is not directly applied to facial surface at the incisal region (201), though masking mixture may penetrate a portion of this region through diffusion. In another embodiment, the masking mixture is applied to a portion of the incisal region, without applying masking mixture to the incisal edge (207).

In other embodiments, two or more masking mixtures having different masking abilities may be applied to a dental prosthesis. In some embodiments, two masking mixtures are used that comprise different concentrations of the same masking agent. In other embodiments, multiple masking mixtures are used that comprise different masking agents each having different masking abilities. For example, a masking mixture may also comprise a colorant to provide greater masking ability when applied to the facial surface.

In a further embodiment, a first masking mixture is applied to the internal surface, and a second masking mixture is applied to a portion of the facial surface that is opposite the internal surface, where the first masking mixture comprises a concentration of masking agent that is less than or equal to the concentration of masking agent in the second masking mixture. In one embodiment, the first masking mixture applied to an internal surface comprises a concentration of masking agent sufficient to mask the visibility of an underlying supporting structure, such as a dark tooth preparation or an implant abutment. In some embodiments, where the ceramic body is highly translucent, the treated internal surface may be visible through the highly translucent facial surface. Therefore, in some embodiments, a second masking mixture having a masking agent concentration that is greater than the first masking mixture may be applied to the facial surface. In this embodiment, the translucency of the facial surface is sufficiently reduced to mask the visibility of first masking agent on the treated internal surface through the facial surface.

Prior to the application of the masking mixture, bisque stage dental prostheses may be unshaded, having the color of natural zirconia materials, which may appear unnaturally white upon sintering if no colorant or staining is applied. Thus, at least one masking mixture may comprise a coloring agent that imparts a dentally acceptable color after sintering when applied to one or more surfaces of the dental prosthesis. Alternatively, shaded bisque stage dental prostheses may be obtained that are made from shaded ceramic powder that provides a dentally acceptable shade upon sintering. In some embodiments, a masking agent applied to the facial surface of a shaded dental prosthesis may alter the final color or shade. Thus, a coloring agent may be added to the masking mixture that is compatible with the shaded ceramic material, and when applied to the facial surface imparts a dentally acceptable shade after sintering. In some embodiments, coloring agents added to the masking mixture may provide additional masking properties to the prosthesis.

In some embodiments, masking mixtures applied to the facial surface and/or internal side surfaces of a prosthesis may penetrate below the surface for a distance of at least 200 μm, or at least 400 μm, or at least 500 μm, or between 200 μm and 800 μm, or between 200 μm and 600 μm, increasing the concentration of masking agent in this region. In one embodiment, the prosthesis comprises a masking agent gradient where the concentration of masking agent (measured as the metal ion of the masking agent) decreases as the distance from a surface to which the masking mixture was applied increases. In one embodiment, a dental prosthesis is provided that comprises at least one masking agent concentration gradient between the facial surface and a region of the internal surface that is opposite the facial surface.

In some embodiments, a concentration gradient of masking agent is achieved in two directions: 1) decreasing masking agent concentration from the internal surface toward a region of the facial surface that is opposite the treated internal surface, and 2) decreasing masking agent concentration from the facial surface towards a region of the internal surface that is opposite the treated facial surface. The concentration of a given masking agent between the facial surface and internal surface is lower than the concentration of masking agent adjacent either the facial surface or internal surface for prostheses having two masking agent concentration gradients. In some embodiments, no metal attributable to the masking agent is present in a detectable level at a distance below and between the facial and internal surfaces.

Additionally, the facial surface of the prosthesis may have a masking agent gradient that decreases from the top two-thirds of the restoration towards the incisal edge when measured near the facial surface. Further, a prosthesis may comprise a masking agent concentration gradient that decreases as the distance from the internal surface increases in the direction of the incisal edge.

Penetration of the masking agent into the ceramic prosthesis may be detected by energy dispersive spectroscopy (EDS) analysis of a cross-section of a dental prosthesis. Points along a line (204) from the facial surface to the internal surface may be analyzed for the concentration of the metal element of the masking agent. In one embodiment, the concentration of metal attributable to the masking agent may be between 0.0001 wt % and 2 wt % when analyzed by EDS according to methods described herein.

Depth of penetration and maskability (measured by a decrease in percent transmission as described herein) may vary between masking agents depending, for example, on selection of ceramic materials, process parameters, and the like. In some embodiments, a first masking agent may be selected that provides greater maskability and lower depth of penetration through the porous zirconia ceramic prosthesis. A second masking agent may be selected that provides greater depth of penetration and lower maskability. A masking gradient may be obtained by applying the masking mixture of two or more masking agents to a dental prosthesis. For example, the first masking agent may provide greater maskability with less diffusion to a first region of the dental prosthesis (e.g., opposite the masking target), and the second masking agent may provide less maskability with greater diffusion through a larger second region (e.g., towards the incisal edge), to provide a masking gradient.

Dental prostheses may comprise zirconia ceramic materials stabilized by 3 mol % to 10 mol % yttria. Yttria-stabilized zirconia ceramic material may be stabilized, for example, from 3 mol % yttria to 7.5 mol % yttria, from 4.0 mol % yttria to 7.5 mol % yttria, from 4 mol % yttria to 7 mol % yttria, from 5 mol % yttria to 8 mol % yttria, from 5 mol % yttria to 7.5 mol % yttria, from 5 mol % yttria to 7 mol % yttria.

Zirconia ceramic material may comprise a mixture of unstabilized zirconia and stabilized zirconia ceramic materials. The term stabilized zirconia ceramic herein includes fully stabilized and partially stabilized zirconia. Specific examples include zirconia with no yttria, or yttria-stabilized zirconia including, but not limited to, commercially available yttria-stabilized zirconia, for example, from Tosoh USA, such as Tosoh TZ-3YS and Tosoh TZ-PX430. The calculated amount of yttria (e.g., yttria mol %) in zirconia ceramic material may vary from 'nominal' values implied by commercial nomenclature (e.g. 3YS). The mol % yttria in zirconia ceramic material may be calculated, for example, based on compositional information received from manufacturer certification.

Dental prosthetic shapes may be formed as green bodies or bisqued state bodies. Green body manufacturing methods may include dry forming processes, such as uniaxial pressing and cold isostatic pressing, and wet forming processes, including but not limited to, pressure-casting, slip-casting, filter pressing, and centrifugal casting methods. A green body manufacturing method such as a slip-casting process, may include the process steps of selecting starting materials; mixing and comminuting the starting materials to form a slurry; and casting the slurry to form a desired green body form, such as the shape of a milling blocks. Methods for making zirconia dental prosthesis materials suitable for use herein may be found in commonly owned patents and patent publications, including U.S. Pat. Nos. 9,434,651, 9,790,129, and U.S. Pat. Pub. 2018/0235847, the subject matter of each is hereby incorporated by reference in its entirety.

Yttria-stabilized zirconia ceramic materials used as starting materials to form millable blocks may, optionally, include a small amount of alumina (aluminum oxide, $Al_2O_3$) as an additive. For example, some commercially available yttria-stabilized zirconia ceramic material include alumina at concentrations of from 0 wt % to 2 wt %, or from 0 wt % to 0.25 wt %, such as 0.1 wt %, relative to the zirconia material. Other optional additives of the ceramic starting material may include coloring agents to obtain shaded zirconia ceramic powder that may be formed by, for example, casting or pressing into shaded ceramic blocks that have a dentally acceptable shade or pre-shade upon sintering. Additives may include, but are not limited to oxides, salts, or other compounds or complexes of metal coloring agents that include erbium, terbium, chromium, cobalt, copper, iron, manganese, nickel, praseodymium, and/or other coloring ions used to obtain desired dental shades in final sintered prostheses, or for example, that match a Vita A1-D4® Classical Shades or bleached shades, and/or to obtain desired opalescence or fluorescence properties for dental applications. In some embodiments coloring compositions may comprise at least one metal selected from, but not limited to, Tb, Er, Cr, Fe, Ni, or Co, and combinations thereof. Still other optional additives include alternative stabilizer materials, such as cerium oxide and/or magnesium oxide. Still other optional additives include grain growth inhibitors, sintering aids, and/or toughening aids.

Manufacturing processes described herein may provide green bodies having relative densities $\rho_R$ greater than 40%, such as from 40% to 65% relative density, or from 52% to 65% relative density, or such as from 56% to 62% relative density. As used herein, the term "relative density" (PR) refers to the ratio of the measured density $\rho_M$ of a sample (g/cm³) to the theoretical density $\rho_T$ for the zirconia ceramic material, provided in Table 1, (i.e., $\rho_R = \rho_M/\rho_T$).

Green bodies may be partially consolidated to obtain bisque stage bodies by heating or firing green bodies, in the shape of blocks to obtain, for example, porous bisqued blocks. In some embodiments, relative densities of bisque blocks do not increase more than 5% over the green body density. Bisquing processes commonly known in the art are suitable for use herein. Bisque firing steps may include heating the green body at an oven temperature of from 800° C. to 1100° C. for a holding period of about 0.25 hours to 3 hours, or about 0.25 hours to 24 hours. In some embodiments, bisque processes comprise heating green bodies in an oven heated at an oven temperature of 900° C. to 1000° C. for 30 minutes to 5 hours. In some embodiments, the difference between the relative densities of the bisque body and the green body is 3% or less. Resulting bisqued bodies may be fully dried and have strength sufficient to withstand packaging, shipping, and, optionally, milling to form a dental prosthesis shape.

A bisque body may have a relative density $\rho_R$ greater than or equal to 40%, such as from 40% to 70%, or from 52% to 68%, or from 54% to 66%, or from 58% to 62%. Bisqued bodies described herein may have a porosity of less than or equal to 60%, such as from 30% to 60%, or from 32% to 48%, or from 38% to 42%. As used herein, the term "porosity", expressed as percent porosity above, is calculated as: percent porosity=1-percent relative density. A dental block for producing a dental prosthesis includes a zirconia bisqued body having a density of between 40% to 65% of theoretical density and having a porosity of between 35% and 60%, such as between 35% and 55%, such as between 35% and 50%, such as between 35% and 45%, such as between 38% and 41%. In some embodiments, the median pore size of bisque bodies is less than 200 nm, or less than 150 nm, or less than 100 nm, such as from 20 nm to 90 nm, or from 35 nm to 85 nm, or from 40 nm to 80 nm, or from 45 nm to 75 nm, or from 50 nm to 90 nm, or from 50 nm to 75 nm, when tested according to the methods described herein. As used herein, the term "median pore diameter" refers to the pore diameter measurements obtained from a bisqued body via mercury intrusion performed with an Autopore V porosimeter from Micromeritics Instrument Corp.

Dental prostheses may be shaped from porous, pre-sintered blocks by conventional subtractive processes, such as milling or machining processes known to those skilled in the art. The blocks may be shaped in a crown, a multi-unit bridge, an inlay or onlay, a veneer, a full or partial denture, or other dental prosthesis.

After treating bisque stage dental prostheses by applying one or more liquid masking mixtures, the bisque stage bodies may be "fully sintered" under atmospheric pressure to a density that is at least 98% of the theoretical density of a sintered body. Sintering may occur at oven temperatures in the range of 1200° C. to 1900° C., or 1400° C. to 1580° C., or 1400° C. to 1450° C. Hold times (dwell times) at a temperature within a sintering temperature range may be from 1 minute to 48 hours, such as from 10 minutes to 5 hours, or from 30 minutes to 4 hours, or from 1 hour to 4 hours, or from 1 hour to 3 hours, or from 2 hours to 2.5 hours. Other sintering processes include multi-step sintering processes described in commonly owned U.S. Pat. Pub. 2019/0127284, filed Oct. 31, 2018, hereby incorporated herein by reference in its entirety. Multi-step sintering processes may comprise one or more temperature gradients within a sintering temperature range, with each gradient having the same or different ramp rates, reaching oven temperatures at or above 1200° C., such as from 1200° C. to 1900° C. Multi-step sintering methods may optionally having no hold time within a sintering temperature range, or one hold time or multiple hold times at or above 1200° C. Multi-step sintering processes may have multiple temperature peaks at or above 1200° C., and at least one temperature steps that is between 25° C. to 600° C. lower, or between 50° C. to 400° C. lower, than a preceding or subsequent temperature peak. Hold times at temperature peaks may be between 0 minutes and 30 minutes, and a lower temperature step between two temperature peaks may have a hold time between 2 minutes and 5 hours.

In one embodiment, the porous form of a zirconia ceramic dental restoration that comprises 4 mol % yttria to 6 mol % yttria is treated with a masking composition to increase maskability to selected regions of the restoration. A masking solution comprising a total concentration of 0.4 wt % to 50 wt % of aluminum chloride hexahydrate, zinc nitrate hexahydrate, or a combination thereof, is applied to the internal surface (e.g., brushing up to 3 times) and a region of the facial surface that is opposite the internal surface (e.g., by brushing up to 4 times). The zirconia restoration may be prepared from a pre-shaded ceramic dental block. The treated zirconia restoration is sintered to greater than 99% theoretical density.

In another embodiment, the porous form of a zirconia ceramic dental restoration comprises 4 mol % yttria to 6 mol % yttria. A first aqueous masking solution is provided that comprises a coloring solution comprising one or more metallic salts of Ni, Fe, Cu, Er, Tb, Co, Cr, Pr and Mn, wherein the total concentration of metallic salt as a coloring agent is from 2 wt % to 15 wt %, and further comprises at least one of 0.4 wt % to 10 wt % aluminum chloride hexahydrate or 4 to 30 wt % zinc nitrate hexahydrate. The first aqueous masking solution is applied to an internal surface (e.g., by brushing up to 3 times) and a region of the facial surface that is opposite the internal surface (e.g., by brushing up to 4 times) of the dental restoration. In a further embodiment, after applying the first masking solution, a second masking solution comprising at least one of 0.4 wt % to 40 wt % aluminum chloride hexahydrate or 5 wt % to 40 wt % zinc nitrate hexahydrate is applied over the first masking solution on the internal surface (e.g., by brushing up to 2 times). The zirconia restoration may be prepared from a pre-shaded or unshaded ceramic dental block. After application of the masking solutions, the treated zirconia restoration is sintered to greater than 99% theoretical density.

In a further embodiment, the porous form of a zirconia ceramic dental restoration comprises 4.5 mol % to 6 mol % yttria. A first aqueous masking solution is provided that comprises a coloring solution comprising one or more metallic salts of Ni, Fe, Cu, Er and Mn, wherein the total concentration of metallic salt as a coloring agent is from 2 wt % to 10 wt %, and further comprises 0.4 wt % to 5 wt % aluminum chloride hexahydrate and 9 to 25 wt % zinc nitrate hexahydrate. The first masking solution is applied to the internal surface of the restoration (e.g., by brushing up to 3 times) and to a region of the facial surface that is opposite the internal surface (e.g., brushing up to 4 times). In a further embodiment, after application of the first masking solution, a second masking solution comprising 0.4 wt % to 20 wt % aluminum chloride hexahydrate and 19 wt % to 40 wt % zinc nitrate hexahydrate is applied over the first masking solution on the internal surface (e.g., brushing up to 2 times). The zirconia restoration may be prepared from a pre-shaded or unshaded-ceramic dental block. After application of the masking solutions, the treated zirconia restoration is sintered to greater than 99% theoretical density.

In one embodiment, a sintered yttria-stabilized zirconia dental prosthesis comprising zirconia stabilized with 4.5 mol % yttria to 7 mol % yttria, is provided having an internal (fitting) surface to which a dental support structure attaches, a facial surface opposite the cavity and an incisal edge, and a masking agent comprising a metal selected from Zn, Ti, Al or a combination thereof. In one embodiment, the prosthesis has a first masking agent concentration gradient through the thickness of the prosthesis, wherein the metal concentration decreases from the facial surface to a distance below the facial surface that is opposite the internal surface, and a second masking agent concentration gradient on the facial surface, wherein the concentration of metal decreases as the distance from the facial surface region opposite the internal surface towards the incisal edge increases, when measured by EDS as described herein.

In some embodiments, the percent transmittance of the treated prosthesis is reduced to less than or equal to about 55% transmittance, or less than or equal to about 50%, when measured at 700 nm on a 1 mm thick sintered ceramic body, and tested by methods provided herein. Moreover, sintered ceramic bodies formed by methods described herein have flexural strength values greater than 500 MPa, greater than 600 MPa, when tested according to methods described herein.

Test Methods
Density

For the examples described herein, density calculations of ceramic bodies were determined as follows. The density of green body blocks were calculated by measuring the weight and dividing by the volume calculated from the dimensions of the green block. The density of bisqued body blocks were determined by liquid displacement methods of Archimedes principle. Flat wafers were sectioned or milled from a bisqued block and dried prior to measuring the dry mass. Samples were then saturated with deionized water under vacuum (29-30 in Hg vacuum pressure) for one hour prior to measuring the suspended and saturated masses. All masses were measured to four decimal points precision. Relative densities of the samples were calculated based on theoretical densities corresponding to yttria content as indicated in Table 1.

TABLE 1

Theoretical Densities Of Yttria-Stabilized Zirconia Composition.

| Yttria (mol %) | Density (g/cm$^3$) |
|---|---|
| 4.0 | 6.080 |
| 5.2 | 6.058 |
| 5.3 | 6.056 |
| 5.4 | 6.054 |
| 5.5 | 6.052 |
| 5.6 | 6.050 |
| 5.7 | 6.048 |
| 5.8 | 6.046 |
| 5.9 | 6.045 |
| 6.0 | 6.043 |
| 6.1 | 6.042 |
| 6.3 | 6.037 |
| 6.4 | 6.035 |
| 6.5 | 6.033 |
| 6.7 | 6.030 |
| 6.8 | 6.028 |
| 6.9 | 6.026 |

TABLE 1-continued

Theoretical Densities Of Yttria-Stabilized Zirconia Composition.

| Yttria (mol %) | Density (g/cm$^3$) |
|---|---|
| 7.0 | 6.025 |
| 7.1 | 6.023 |
| 7.4 | 6.019 |
| 7.9 | 6.011 |
| 8.4 | 5.958 |
| 9.7 | 5.923 |

For purposes herein, a ceramic material that is fully sintered has a density that is about 98%, or greater, of the theoretical density.

Translucency

Sintered body translucency was determined by measuring the percent transmittance of D65 light at a wavelength of 700 nm from a 0.95 to 1.05 mm thick sintered sample. Translucency wafers were sectioned or milled from a bisqued block and machined to a diameter corresponding to a final diameter of approximately 30 mm after sinter. The wafers were then ground flat until visually free of defects with 1200 grit and 2000 grit SiC polishing paper. The final bisqued thickness corresponded to 1 mm after sintering and polishing. Samples ground to the desired shape were removed of surface dust and then sintered according to the sintering profile(s) described herein.

After sintering, the samples were polished prior to testing. A polishing procedure was performed using three separate polishing diamond suspensions to remove scratches, 15 µm, 3 µm, and 1 µm, at a rotating speed of 300 rpm for a dwell time of about 5 to 15 minutes, using hand pressure (approximately 2 to 3 pounds).

Total transmittance spectra were measured between the wavelengths of 360 nm to 740 nm with a Konica-Minolta CM5 spectrophotometer illuminated by a D65 light source for all samples. Information contained in the data tables herein refer to measurements at 700 nm or 500 nm wavelengths, as indicated, which are extracted from these measurements. The spectrophotometer was calibrated to white and black prior to measurement. Translucency samples were placed flush against the (approximately) 25 mm integrating sphere aperture. A minimum of two spectra were collected per sample and averaged to yield a final measured transmittance spectra (S-TM). Collected transmittance data may be reported as "percent (%) transmittance".

Opacity Measurement

Wafers with a thickness of 1±0.05 mm, polished according to the Translucency Test Method, were measured between the wavelength of 400 nm to 700 nm with a Konica-Minolta CM5 spectrophotometer at opacity mode (reflection mode; Specular Component type: SCI; Measurement area diameter=8 mm) illuminated by a D65 light source for all samples. Before testing, the machine was calibrated. The wafers were measured under the white and dark background. A white calibration tile (Avian Technologies LLC, FWT-99-02C) was used for the white background. The dark background using a zero calibration box (Konica Minolta, CM-A124). A minimum of two spectra were collected per sample and averaged to yield the final measured opacity.

Spectral Image Data

Spectral image data of the labial faces of glazed crowns and wafers were collected using a SpectroShade® Micro II imaging spectrophotometer. Prior to testing, the Spectro- Shade® Micro II imaging spectrophotometer was calibrated using the white and green tiles on the docking base provided by the manufacturer. Sample crowns were imaged over a dark background (the AC/DC switching adaptor supplied with the device; Mean Well Enterprises, GS40A15-P1M). A small dot of wax was used to support the sample crown by the cingulum upon the dark background, such that the labial face was approximately level with the dark background surface and exposed for spectral imaging. Wafers were placed flat upon the dark background for L* value measurement. The SpectroShade® Micro II device (with mouthpiece attached) was then aligned by hand to capture a spectral image measurement file for each sample crown and wafer.

Figure 9:
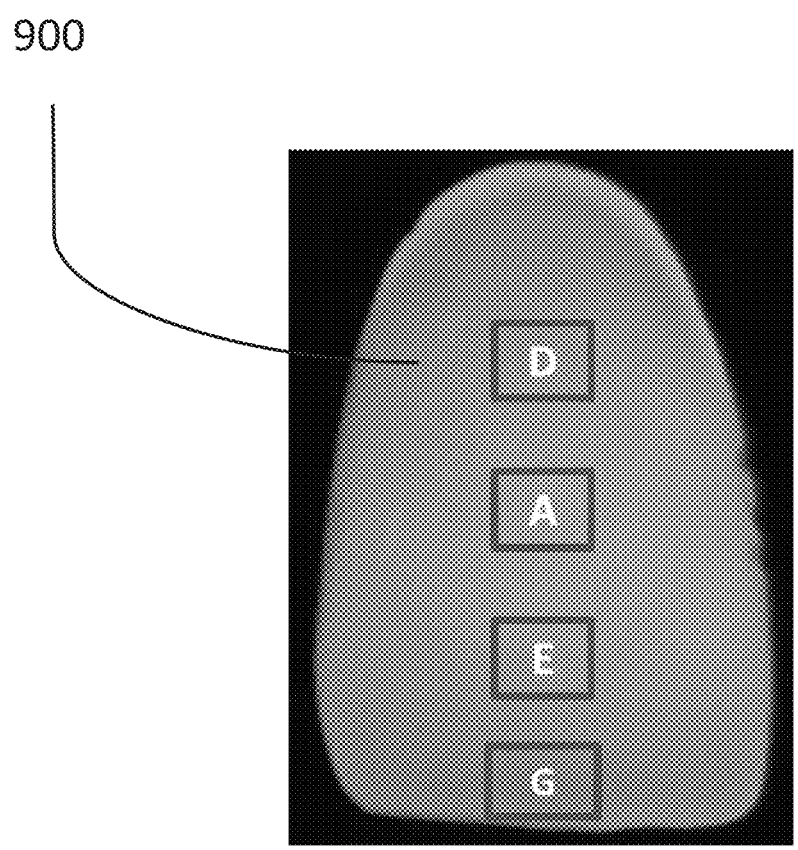
FIG. 9 is a spectral image of a crown showing locations used to measure perceptual lightness (L*) values used to calculate Lightness Measurement Slope Values (LMSV) as described herein.

SpectroShade® Micro II measurement files were then uploaded to a PC and analyzed using the SpectroShade® Analysis software. For each wafer, an L*a*b* color space value array was collected from the center of each wafer using a cursor size setting of 50 within the SpectroShade® Analysis software (corresponding to an area of 1.6 mm×1.6 mm on the wafer surface). With reference to FIG. 9, for each sample crown 900, L*a*b* color space value averages were collected from four areas (designated D, A, E, and G). Areas D, A, and E were each set with a cursor size setting of 50 within the SpectroShade® Analysis software (corresponding to an area of 1.6×1.6 mm on the sample crown face). Area G correspond to an area approximately 0.3×2 mm. The locations of areas D, A, E, and G are determined by reference to the distance between the incisal and gingival edges of the crown sample, with the relative distance from the incisal edge to the center of each area being: Area D—69%, Area A—46%, Area E—27%, and Area G—8%.

Shade Matching Evaluation

Shade evaluation and shade matching was performed by visual method using a full-spectrum balanced light source, the CIE Standard Illuminant D50 with a correlated color temperature (CCT) of 5000 K. Shaded, fully sintered zirconia ceramic bodies prepared by methods disclosed herein were visually evaluated by the unaided eye under the light source to confirm shade matching to a target shade of the Vita Classical A1-D4® Shade Guide (containing shades B1, A1, B2, D2, A2, C1, C2, D4, A3, D3, B3, A3.5, B4, C3, A4, C4, as arranged by brightness (value), and Vita Bleached Shades.

X-Ray Diffraction (XRD)

The crystal phase of bisque state zirconia ceramic bodies were measured by X-Ray diffractometer (XRD, Rigaku SmartLab, Japan), using CuKα radiation. The measurement conditions were as follows: radiation source: CuKα ($\lambda$=1.541862 Å); measurement mode: step scanning; scanning condition: 1° per minute; step width: 0.02 deg; scattering slit: 5.0 deg; scattering slit: 5.0 deg; receiving slit #1: 4.0 deg; receiving slit #2: 13.0 mm; scanning mode: continuous mode; and scanning range (2θ): 20°-80°.

By analyzing an XRD pattern, tetragonal (t)-cubic (c) phase ratio was calculated by Equation (1)

$$(t + c) \text{ phase ratio (\%)} = 100 - f_m \quad (1)$$

where, $f_m$ is the crystal ratio (%) of monoclinic phase (m), obtained by Equation (2)

$$f_m(\%) = \frac{I_m(111) + I_m(11\bar{1})}{I_m(111) + I_m(11\bar{1}) + I_c(111) + I_t(101)} \times 100 \quad (111)$$

where, $I_m(111)$ is the XRD peak intensity of the monoclinic phase (111) plane; $I_m(11\bar{1})$ is the XRD peak intensity of the monoclinic phase (11$\bar{1}$) plane; $I_t(101)$ is the XRD peak intensity of the tetragonal phase (101) plane; and $I_c(111)$ is the XRD peak intensity of the cubic phase (111) plane, and, where XRD peak intensities were measured with background removed.

Mercury Porosimetry

Pore size and pore size distributions were measured on a 1 gram to 4 gram sample obtained from a bisqued block. Samples were dried before mercury intrusion. Intrusion was performed with a Micromeritics Autopore V porosimeter with set pressure ranges from total vacuum to 60,000 psi using Micromeritics penetrometers models #07 and #09. The median pore diameter (volume) from the measurement was reported as the Median pore diameter.

EXAMPLES

Ceramic Materials Preparation

Yttria-stabilized zirconia ceramic bodies stabilized with approximately 4.7 mol %, 5.3 mol % and 5.8 mol % yttria, were treated and prepared as follows.

Bisque stage yttria-stabilized zirconia ceramic blocks were prepared comprising approximately 4.7 mol % yttria and 5.8 mol % yttria. The bisque stage bodies had between about 52% and 65% theoretical density, and a pore size of D50=50 nm to 60 nm.

Yttria-stabilized zirconia having 4.7 mol % yttria was prepared by a colloidal casting process for casting a ceramic slurry to form a cast block. The ceramic slurries contained a combination of two zirconia powders stabilized with approximately 3 mol % yttria and approximately 5 mol % yttria (commercially available through Tosoh USA, Inc. Grove City, OH). The two zirconia powders were combined in a weight ratio to arrive at an yttria-stabilized zirconia comprising 4.7 mol % yttria. The slurry was prepared and cast substantially according to methods described in commonly owned U.S. Pat. Pub. 2018/0235847, hereby incorporated herein in the entirety.

Yttria-stabilized zirconia having 5.8 mol % yttria was prepared by a colloidal casting process for casting a ceramic slurry to form a cast block. The ceramic slurries contained a combination of two yttria-stabilized zirconia powders comprising approximately 5 mol % yttria and approximately 8 mol % yttria (commercially available through Tosoh USA, Inc. Grove City, OH), in a weight ratio to arrive at a yttria-stabilized zirconia comprising 5.8 mol % yttria. The slurry was prepared and cast substantially according to methods described in commonly owned U.S. Pat. Pub. 2018/0235847.

After casting, the 4.7 mol % yttria-stabilized zirconia blocks and the 5.8 mol % yttria-stabilized zirconia ceramic blocks were heated in an oven to a bisque stage according to the heating profile of Table 2.

TABLE 2

Bisquing Profile For 4.7 Mol % and 5.8 Mol % Yttria-Stabilized Zirconia Blocks.

| Time (min) | Temp (° C.) |
|---|---|
| — | 25 |
| 70 | 60 |
| 190 | 60 |
| 590 | 80 |

TABLE 2-continued

Bisquing Profile For 4.7 Mol % and 5.8 Mol %
Yttria-Stabilized Zirconia Blocks.

| Time (min) | Temp (° C.) |
|---|---|
| 710 | 80 |
| 1310 | 110 |
| 1430 | 110 |
| 1683 | 300 |
| 2022 | 950 |
| 2382 | 950 |
| * | ambient |

*Natural cool down

Bisque stage yttria-stabilized zirconia ceramic blocks were prepared that comprised approximately 5.3 mol % yttria by pressing zirconia powder (ZPex Smile from Tosoh), and heated to achieve a theoretical density of approximately 52%, and approximate pore size of D(50)=80 nm.

Sintering Profiles

Ceramic bodies (e.g., wafers) comprised of 4.7 mol % yttria-stabilized zirconia, 5.3 mol % yttria-stabilized zirconia and 5.8 mol % yttria-stabilized zirconia were treated with masking mixtures according to the examples provided below, and then were sintered according to the sintering profile of Table 3.

TABLE 3

Sintering Profile For 4.7 Mol %, 5.3 Mol % and
5.8 Mol % Yttria-Stabilized Zirconia Bodies.

| 4.7 Mol % Yttria | | 5.3 Mol % Yttria | | 5.8 Mol % Yttria | |
|---|---|---|---|---|---|
| Time (min) | Temp (° C.) | Time (min) | Temp (° C.) | Time (min) | Temp (° C.) |
| — | 25 | — | 25 | — | 25 |
| 78 | 1100 | 78 | 1200 | 65 | 1000 |
| 138 | 1100 | 138 | 1200 | 290 | 1450 |
| 188 | 1200 | 188 | 1300 | 320 | 1530 |
| 213 | 1450 | 211 | 1530 | 350 | 1530 |
| 214 | 1200 | 361 | 1530 | 430 | 150 |
| 304 | 1200 | 451 | 150 | * | ambient |
| 322 | 1475 | * | ambient | | |
| 327 | 1475 | | | | |
| 335 | 1550 | | | | |
| 345 | 1550 | | | | |
| 435 | 150 | | | | |
| * | ambient | | | | |

*natural cool down

Sintered ceramic materials comprised of highly translucent yttria-stabilized zirconia ceramic material were treated with multiple concentrations of masking mixtures in the bisque stage to reduce translucencies after sintering.

Bisque yttria-stabilized zirconia ceramic bodies comprised of either 4.7 mol % yttria, 5.3 mol % yttria or 5.8 mol % yttria, were treated with masking mixtures prepared as follows. Masking mixtures were prepared by mixing water and 10 wt %, 20 wt % or 30 wt % of masking agents aluminum chloride hexahydrate ($AlCl_3 \cdot 6H_2O$) (commercially available through Alfa Aesar) and zinc sulfate heptahydrate ($ZnSO_4 \cdot 7H_2O$) commercially available through Sigma Aldrich), as specified in Table 4. The weight percent of the masking agent in solution and the concentration of the metal ion (Al or Zn) of the masking agent in the solution (as ppm), are also reported in Table. 4.

Wafers were milled from the bisque stage zirconia blocks to a target sintered thickness of 1 mm. Liquid masking mixtures were applied to the wafers by painting front and back surfaces three time each.

The sample wafers were sintered according to methods provided in Table 3, and prepared for transmittance measurements according to the test method provided herein. Total transmittance measurements are reported for 500 nm and 700 nm Table 4. Control samples of each zirconia composition without a masking material had a percent transmittance at 700 nm of 57% (4.7 mol % yttria and 5.3 mol % yttria), and 68% (5.8 mol % yttria).

TABLE 4

Translucency Of Yttria-Stabilized Zirconia With Masking Agent.

| | Liquid Masking Mixture | | | % Transmittance | |
|---|---|---|---|---|---|
| Example # | Masking Agent | Wt % | Metal (g/L H2O) | T % @ 500 nm | T % @ 700 nm |
| 4.7 Mol % Yttria-Stabilized Zirconia control: | | | | — | 57 |
| 1 | $AlCl_3 \cdot 6H_2O$ | 10% | 12.4 | 46.3 | 53.7 |
| 2 | $AlCl_3 \cdot 6H_2O$ | 20% | 27.9 | 42.6 | 49.9 |
| 3 | $AlCl_3 \cdot 6H_2O$ | 30% | 47.9 | 40.2 | 47.5 |
| 4 | $ZnSO_4 \cdot 7H_2O$ | 10% | 25.3 | 48.1 | 56.0 |
| 5 | $ZnSO_4 \cdot 7H_2O$ | 20% | 56.8 | 46.3 | 54.8 |
| 6 | $ZnSO_4 \cdot 7H_2O$ | 30% | 97.4 | 42.9 | 51.1 |
| 5.3 Mol % Yttria-Stabilized Zirconia control: | | | | — | 57 |
| 7 | $AlCl_3 \cdot 6H_2O$ | 10% | 12.4 | 42.2 | 50.3 |
| 8 | $AlCl_3 \cdot 6H_2O$ | 20% | 27.9 | 39.9 | 47.8 |
| 9 | $AlCl_3 \cdot 6H_2O$ | 30% | 47.9 | 37.4 | 44.9 |
| 10 | $ZnSO_4 \cdot 7H_2O$ | 10% | 25.3 | 46.0 | 54.5 |
| 11 | $ZnSO_4 \cdot 7H_2O$ | 20% | 56.8 | 31.1 | 36.6 |
| 12 | $ZnSO_4 \cdot 7H_2O$ | 30% | 97.4 | 29.1 | 33.5 |
| 5.8 Mol % Yttria-Stabilized Zirconia control: | | | | — | 68 |
| 13 | $AlCl_3 \cdot 6H_2O$ | 10% | 12.4 | 46.7 | 55.3 |
| 14 | $AlCl_3 \cdot 6H_2O$ | 20% | 27.9 | 44.9 | 52.3 |
| 15 | $AlCl_3 \cdot 6H_2O$ | 30% | 47.9 | 43.0 | 50.2 |
| 16 | $ZnSO_4 \cdot 7H_2O$ | 10% | 25.3 | 48.2 | 59.1 |
| 17 | $ZnSO_4 \cdot 7H_2O$ | 20% | 56.8 | 41.4 | 48.8 |
| 18 | $ZnSO_4 \cdot 7H_2O$ | 30% | 97.4 | 36.3 | 42.8 |

Percent transmittance was reduced between 1% and 25% for all test sample zirconia materials for each masking mixture throughout the concentration range tested, when compared to the untreated zirconia control samples.

Sintered, 5.8 mol % yttria-stabilized zirconia ceramic bodies treated Al- or Zn-containing masking mixtures in the bisque stage were analyzed by scanning electron microscopy at ×5000 magnification. FIGS. 3A, 3B and 3C are SEM images of 5.8 mol % yttria-stabilized sintered zirconia ceramic bodies treated with masking mixtures comprising 10 wt %, 20 wt % and 30 wt % of zinc sulfate heptahydrate, respectively. FIGS. 4A, 4B, and 4C are SEM images of sintered 5.8 mol % yttria-stabilized zirconia ceramic bodies treated with masking mixtures comprising 10 wt %, 20 wt % and 30 wt % of aluminum chloride hexahydrate, respectively.

Example 19 Through Example 25

Masking mixtures were prepared and applied to bisque stage bodies of highly translucent zirconia ceramic materials stabilized by 5.8 mol % yttria to reduce translucencies after sintering.

Bisque stage 5.8 mol % yttria-stabilized zirconia ceramic materials were prepared substantially as described above. Masking mixtures were prepared by mixing water and masking agents as specified in Table 5; weight percent of the masking agent and concentration of the metal ion (ppm) in solution is reported. Masking mixtures were applied by painting three times on front and back surfaces of wafers of bisque stage zirconia bodies that were milled to a target sintered thickness of 1 mm. The samples were sintered according to Table 3.

Transmittance measurements at 500 nm and 700 nm are reported in Table 5. The percent transmittance of a control sample of 5.8 mol % yttria-stabilized zirconia without a masking agent at 700 nm was 57% for a 1 mm thick sintered body.

TABLE 5

Masking Mixtures And Translucency Measurements Of 5.8 Mol % Yttria-Stabilized Zirconia Treated With Masking Agents.

| Example # | Liquid Masking Mixture | | Metal (g/L H2O) | % Transmittance | |
|---|---|---|---|---|---|
| | Masking Agent | Wt % | | 500 nm | 700 nm |
| 19 | $ZnSO_4 \cdot 7H_2O$ | 20% | 56.8 | 44.9 | 53.3 |
| 20 | $La(NO_3)_3 \cdot 6H_2O$ | 20% | 80.2 | 53.4 | 63.8 |
| 21 | $Ti[O(CH_2)_3CH_3]_4$ | 20% | 35.2 | 51.0 | 62.1 |
| 22 | $Ca(NO_3)_2 \cdot 4H_2O$ | 20% | 42.4 | 47.1 | 56.4 |
| 23 | $ZnSO_4 \cdot 7H_2O$ | 50% | 227.4 | 30.1 | 34.3 |
| 24 | $La(NO_3)_3 \cdot 6H_2O$ | 50% | 320.8 | 48.5 | 58.7 |
| 25 | $Ti[O(CH_2)_3CH_3]_4$ | 50% | 140.7 | 45.6 | 55.0 |

Application of the masking agents resulted in a decrease in percent transmittance, reported in Table 5, for Examples 19, 22, 23, and 25. Examples 20, 21 and 24, did not show a decrease in percent transmittance compared to the control.

Example 26 Through Example 28

Masking mixtures were prepared and applied to bisque stage bodies of highly translucent zirconia ceramic materials stabilized by 5.8 mol % yttria to test for a reduction in flexural strength after sintering.

In Examples 26 through 28, ceramic bodies also comprising 5.8 mol % yttria-stabilized zirconia were treated by painting 3 times on each side with a liquid masking agent. After sintering, the samples were measured to determine whether application of the masking agent decreased flexural strength of sintered, yttria-stabilized zirconia bodies. The composition of the liquid masking mixtures and flexural strength testing results (with standard deviations (STD A-MPA)) for Examples 26 through 29 are reported in Table 6.

TABLE 6

Masking Mixtures And Flexural Strength Of 5.8 Mol % Yttria-Stabilized Zirconia Bodies Treated With Masking Agents

| Example # | Liquid Masking Mixture | | Metal (g/L H2O) | Flexural Strength- MPa | STD Δ- MPa |
|---|---|---|---|---|---|
| | Masking Agent | Wt %. | | | |
| 26 | $ZnSO_4 \cdot 7H_2O$ | 15% | 40.1 | 650 | 99 |
| 27 | $Ti[O(CH_2)_3CH_3]_4$ | 20% | 35.2 | 635 | 112 |
| 28 | $Ti[O(CH_2)_3CH_3]_4$ | 30% | 60.3 | 717 | 96 |

Flexural strength measurement of an untreated control sample of 5.8 mol % yttria-stabilized zirconia was approximately 620 MPa. No decrease in strength was measured where the flexural strength measurements of all samples treated with a masking agent were greater than the control.

Example 29 Through Example 33

Masking mixtures were prepared and applied to bisque stage bodies of highly translucent zirconia ceramic materials stabilized by 5.8 mol % yttria to test for a change in hardness after sintering.

In Examples 29 through 33, ceramic bodies comprising 5.8 mol % yttria-stabilized zirconia were treated by dipping in a liquid masking agent. After sintering, the samples were measured to determine the effect of the masking agent on the hardness of sintered, yttria-stabilized zirconia bodies. Multiple liquid masking mixtures were prepared at weight percent concentrations of 10 wt %, 20 wt %, 30 wt % and 50 wt %, based on the weight of the masking agent in solution. The composition of the liquid masking mixtures and testing results for Examples 29 through 33 are reported in Table 7.

TABLE 7

Hardness Of 5.8 Mol % Yttria-Stabilized Zirconia Bodies With Masking Agents.

| Ex. # | Masking Mixture | Hardness (GPa) | | | |
|---|---|---|---|---|---|
| | | 10 wt % | 20 wt % | 30 wt % | 50 wt % |
| 29 | $ZnSO_4 \cdot 7H_2O$ | 12.9 | 13.3 | 12.9 | 13.0 |
| 30 | $La(NO_3)_3 \cdot 6H_2O$ | 13.4 | 13.4 | 13.4 | 13.2 |
| 31 | $Ti[O(CH_2)_3CH_3]_4$ | 13.3 | 13.4 | 13.4 | 13.5 |
| 32 | $Ca(NO_3)_2 \cdot 4H_2O$ | 13.5 | 13.0 | 13.3 | — |
| 33 | $Sr(NO_3)_2$ | 13.3 | 13.1 | 12.7 | — |

Untreated control samples of sintered 5.8 mol % yttria-stabilized zirconia ceramic bodies had a hardness value of 13.4. A comparison of control samples and test samples for Examples 29-33 showed no decrease in hardness for most samples treated with masking mixtures containing La and Ti, and a slight decrease in hardness for some samples treated with masking mixtures comprising Zn-, Ca- and Sr-containing masking agents.

Examples 34 and 35

Highly translucent yttria-stabilized zirconia ceramic bodies prepared with a masking mixture comprising a combination of Al- and Zn-containing masking agents were tested for hardness after sintering, and compared to ceramic bodies treated with a masking mixture comprising a single masking agent.

Bisque stage 5.8 mol % yttria-stabilized zirconia ceramic bodies were painted three times per side with one of two aqueous masking solutions. A first masking solution comprised 33 gram of $Zn(NO^3)_2 \cdot 6H_2O$ per liter of water; a second masking solution comprised a combination of masking agents, specifically, 33 gram of $Zn(NO^3)_2 \cdot 6H_2O$ and 11.2 gram of $AlCl_3 \cdot 6H_2O$ per liter of water. After painting, the bisque stage bodies were sintered.

Samples were prepared for flexural strength and transmittance testing according to the methods provided herein. The results of flexural strength and percent transmittance at 500 nm and 700 nm are reported in Table 8.

TABLE 8

Flexural Strength And Transmittance Of 5.8 mol % Yttria-Stabilized Zirconia Treated With Zinc And Aluminum-Containing Masking Mixtures.

| Ex. # | Liquid Masking Mixture Wt % | Metal (g/L H2O) | Flexural Strength (MPa) | % Trans. @ 500 nm | % Trans. @ 700 nm |
|---|---|---|---|---|---|
| Control | None | None | 624 ± 27 MPa; | 54.7 | 67.2 |
| 34 | 15 wt % Zn(NO3)2-6H2O | 33 | 642 ± 57 MPa; n = 7 | 48.2 | 60.1 |
| 35 | 15 Wt % Zn(NO3)2-6H2O + 10 wt % $AlCl_3 \cdot 6H_2O$ | 33 + 11.2 | 610 ± 73 MPa; n = 7 | 41.4 | 48.8 |

Sintered ceramic bodies treated with masking mixtures comprising either a single masking agent or two masking agents were found to have no significant change in flexural strength when compared to untreated controls of sintered 5.8 mol % yttria-stabilized zirconia ceramic bodies. Both samples had a decrease in percent transmittance (at 500 nm and 700 nm) compared to the control sample, with the masking mixture comprising two masking agents having a greater decrease in transmittance.

Examples 36 and 37

Sintered yttria-stabilized zirconia prostheses were prepared with a masking agent and then tested for penetration of masking agent by EDS analysis.

Bisque stage dental prostheses were milled from bisque stage 5.8 mol % yttria-stabilized zirconia blocks, and treated with masking solutions with and without coloring solution, as described herein. A first masking mixture was prepared comprising an aqueous solution of 40 wt % $AlCl_3 \cdot 6H_2O$, with no colorant. For Example 36, with reference to FIG. 2, the first masking mixture was applied to approximately the top two-thirds (205, 206) of the facial surface (202) of the crown of when measured on the facial surface from the top (crown margin) (208) towards the bottom (incisal edge) (207). The first masking mixture was applied to the facial surface (202) that is opposite the internal side surface (203), by painting two times by brushing, and the internal bottom surface (212) and internal side surface (203), the facial surface at the incisal region (201) and incisal edge (207) were not treated. The treated samples were dried and sintered to full theoretical density.

Figure 5:
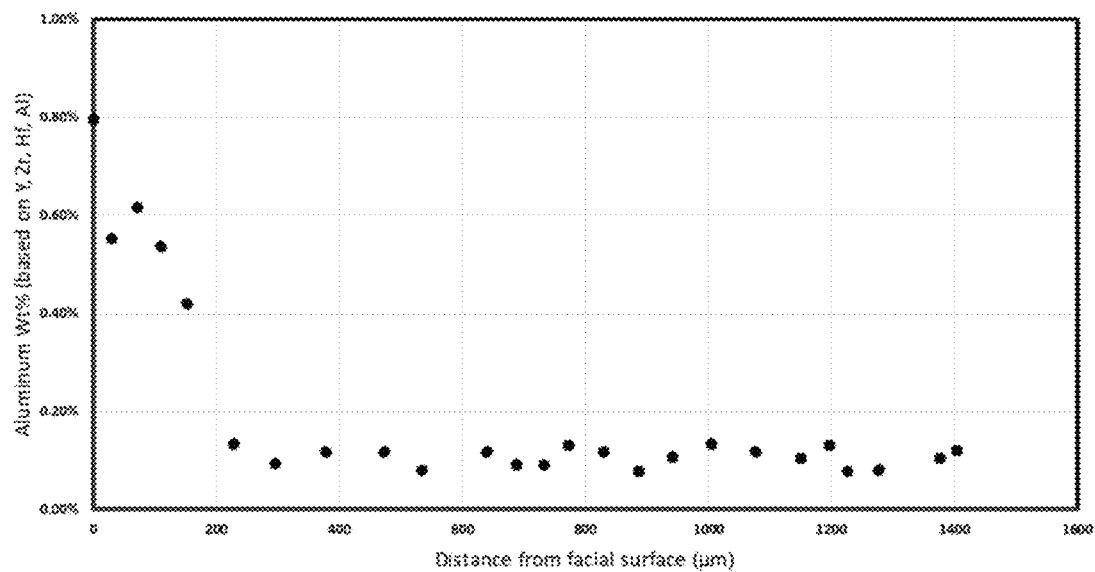
FIG. 5 is a graphical representation of a masking agent concentration through the thickness of a dental prosthesis according to one embodiment.

EDS analysis was conducted using Aztec software, and by the ZAF method as a default matrix correction method with the following parameter settings: voltage-15 kV; current-1.6 nA; measure distance-4.7 mm. For Example 36, penetration of the masking agent through the crown thickness was measured by EDS analysis at sample points along a line (204) from the facial surface to the internal (fitting) surface. The concentration of the masking agent was measured as the weight percent of Al, based on the total amount of Y, Zr, Hf and Al detected by EDS analysis for the sample. Results are reported in Table 9, and illustrated in FIG. 5.

TABLE 9

Concentration Gradient Of Aluminum In A Sintered Body Treated With Aluminum Masking Agent.

| Distance (μm) | Wt % |
|---|---|
| 0 | 0.80% |
| 29.23 | 0.55% |
| 71.94 | 0.62% |
| 110.2 | 0.54% |
| 151.5 | 0.42% |
| 227.1 | 0.13% |
| 294.5 | 0.09% |
| 377.7 | 0.12% |
| 472.2 | 0.12% |
| 532.8 | 0.08% |
| 638.5 | 0.12% |
| 688 | 0.09% |
| 732.9 | 0.09% |
| 771.2 | 0.13% |
| 829.6 | 0.12% |
| 885.8 | 0.08% |
| 942 | 0.11% |
| 1005 | 0.13% |
| 1077 | 0.12% |
| 1151 | 0.11% |
| 1196 | 0.13% |
| 1225.2 | 0.08% |
| 1276.9 | 0.08% |
| 1375.82 | 0.11% |
| 1402.8 | 0.12% |

Aluminum concentrations attributable to the masking solution were detected through a portion of the thickness of the prosthesis below the treated surface. Analysis showed a decrease in aluminum concentration from the facial surface to a depth of approximately 200 μm below the surface.

Additional points on the prosthesis cross-section (200) were analyzed for aluminum concentrations, specifically, a point (209) on the incisal region (201), a point (210) on the facial surface opposite the internal (fitting) surface, and a point (211) on the untreated internal surface that is opposite the facial surface on which the masking mixture was applied. Concentrations of Al from the masking agent are reported in Table 10 as weight percent (wt %) and atom percent (atom %) based on the total amount of Y, Zr, Hf and Al detected.

TABLE 10

Concentration Of Aluminum In A Sintered Body Treated With Aluminum Masking Agent.

| Measurement Location | Wt % | Atom % |
|---|---|---|
| Incisal Region (209) | 0.22 | 0.72 |
| Facial Surface (210) | 0.66 | 2.23 |
| Fitting Surface (211) | 0.14 | 0.47 |

The sample point analyzed on the facial surface (210) showed the highest concentration of aluminum attributable from the masking mixture. The concentration of aluminum in the incisal region where the masking mixture was not applied, and the concentration on the fitting surface were lower than the facial surface to which a masking solution was applied.

For Example 37, a second prosthesis was treated with both the first masking mixture and a second masking mixture. The second masking mixture comprised an aqueous solution of 20 wt % AlCl₃ hexahydrate, and coloring agents comprising 20 wt % iron nitrate nonahydrate, 7.5 wt % nickel nitrate hexahydrate, 1.2 wt % copper chloride dehydrate, and 10.1 wt % erbium nitrate hexahydrate based on the total weight of H₂O in the system. A wetting agent, polyethylene glycol, was added to increase the penetration depth of the masking mixture.

Figure 6:
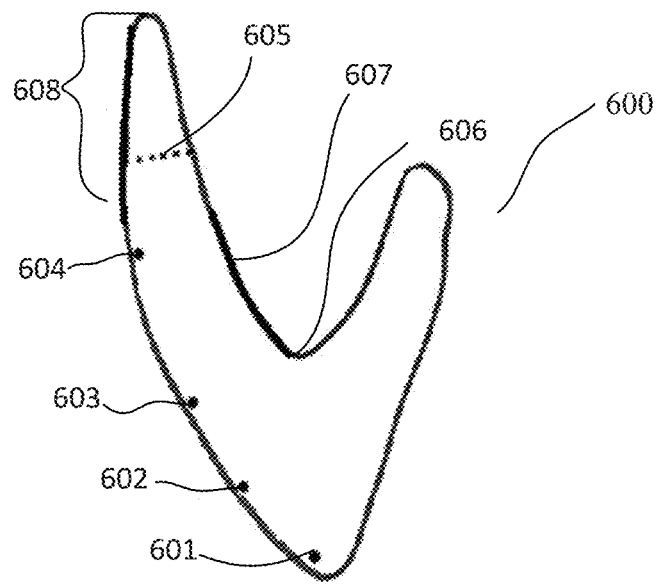
FIG. 6 is an illustrative representation of a cross-sectional view of a dental prosthesis according to one embodiment.

With reference to FIG. 6, the prosthesis was treated by applying the first masking mixture to the internal side surface (607) and internal bottom surface (606) (fitting surfaces) by painting one time. The second masking mixture (comprising coloring agents) was applied to the facial surface. The prosthesis was sintered to full theoretical density and cross-sectional samples were obtained and tested for penetration of the masking agent by EDS analysis. Multiple points were tested along the line (605) through the thickness of the prosthesis between the facial surface and the fitting surface on the top third (608) of the prosthesis nearest the margin. The prosthetic was sampled from the facial surface (approximately 0 μm) towards the internal surface (approximately 1600 μm). Concentrations of Al and Fe from the masking agents were calculated as weight percent (wt %) based on the total amount of Y, Zr, Hf, Fe and Al, and graphically represented in FIGS. 7 and 8.

Figure 7:
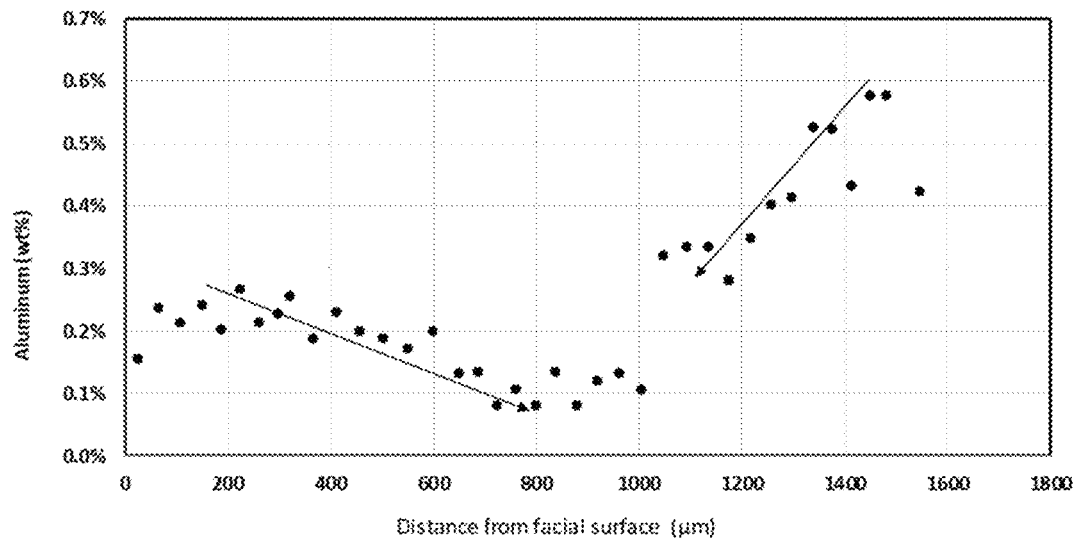
FIG. 7 is a graphical representation of a masking agent concentration through the thickness of a dental prosthesis according to one embodiment.

As illustrated in FIG. 7, two concentration gradients of aluminum were detected through the cross-section. The concentration of aluminum was elevated at both the facial surface and at the internal side surface that were treated with either the first or second masking solutions, respectively. Masking solutions penetrated for a distance of up to about 600 μm below the facial and internal surfaces. The thickness of the prosthesis was approximately 1600 μm between the facial and fitting surface where tested; no increase in aluminum was detected at a distance between about 600 μm and 1000 μm below the facial or internal surfaces.

Figure 8:
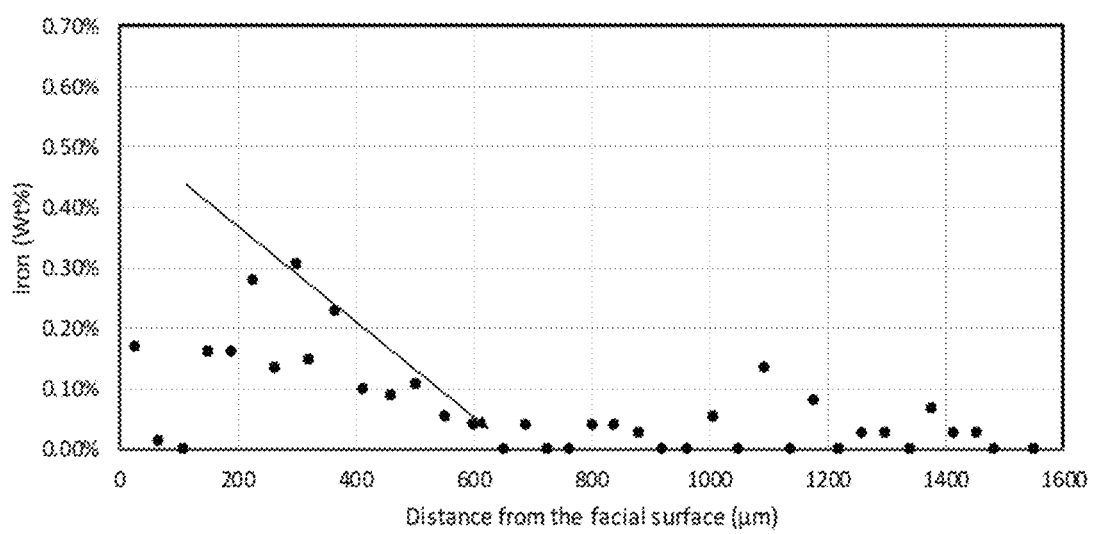
FIG. 8 is a graphical representation of a masking agent concentration through the thickness of a dental prosthesis according to one embodiment.

The concentration of iron was also measured for points along line 605. As illustrated in FIG. 8, a concentration gradient of iron attributable to the coloring solution was detected wherein the concentration of iron decreased as the distance from the facial surface increased.

As illustrated in FIG. 6, concentrations of masking agent were also tested, at multiple locations on the facial surface of the prosthesis (600) at a point on the incisal edge (601), two points above the incisal edge (602, 603) that are below the level of the internal bottom surface (606), and one point on the facial surface opposite the internal side surface (607).

TABLE 11

Concentration Of Aluminum In A Sintered Body Treated With Aluminum Masking Agent.

| Measurement Location | Wt % | Atom % |
|---|---|---|
| Incisal Edge (601) | 0.16 | 0.51 |
| Upper Incisal Third (602) | 0.17 | 0.60 |
| Middle Third - Below Fitting surface (603) | 0.17 | 0.60 |
| Middle Third - Above Fitting Surface (604) | 0.21 | 0.21 |
| Upper Third (605) | 0.24 | 0.80 |

The apparent concentrations, weight percent (wt %) of Al, and atom percent of Al reported in Table 11 indicate a decrease in concentration as the distance from the incisal edge increases.

Example 38 Through Example 41

Translucent zirconia ceramic materials were prepared to determine the relationship between measured perceptual lightness (L*) values and measured translucency (T %) values.

Bisque yttria-stabilized zirconia ceramic bodies comprised of either 3 mol % yttria, 4.7 mol % yttria, 5.3 mol % yttria, or 5.8 mol % yttria were prepared. Wafers were milled from the bisque stage zirconia blocks to a target sintered thickness of 1 mm. The sample wafers were sintered according to the methods provided in Table 3, and prepared for transmittance measurements and spectral image data according to the test methods provided herein. L* value against dark background measurements and total transmittance measurements for 700 nm wavelength light are reported in Table 12.

TABLE 12

Relationship Between Perceptual Lightness (L*) And Transmittance Of Yttria-Stabilized Zirconia.

| Ex. # | Yttria (mol %) | L* Value Measured at Dark Background | % Trans. @700 nm |
|---|---|---|---|
| 38 | 3 | 77.61 | 50% |
| 39 | 4.7 | 75.22 | 55% |
| 40 | 5.3 | 72.88 | 56% |
| 41 | 5.8 | 65.73 | 66% |

Comparison of perceptual lightness (L*) values against transmittance (% T) for the zirconia samples having the tested levels of yttria-stabilization revealed a strong inverse relationship between L* values and % Transmittance values for each sample. At low yttria concentrations (e.g., 3Y), perceptual lightness (L*) values are higher and % transmittance values are lower. At higher yttria concentrations (e.g., 5.8Y), perceptual lightness (L*) values are lower and % transmittance values are higher. Accordingly, each parameter is useful for assessing relative optical performance of translucent zirconia ceramic materials.

Example 42 Through Example 53

Translucent zirconia ceramic materials were prepared to determine the relationship between measured perceptual lightness (L*) values and sample thickness.

Bisque yttria-stabilized zirconia ceramic bodies comprised of 3 mol % yttria and 5.8 mol % yttria were prepared. Wafers were milled from the bisque stage zirconia blocks to a target sintered thicknesses reported in Table 13. The sample wafers were sintered according to the methods provided in Table 3, and prepared for spectral image data analysis according to the test methods provided herein. L* value measurements against a dark background are reported in Table 13.

TABLE 13

Perceptual Lightness (L*) of Yttria-Stabilized Zirconia Samples.

| Ex. # | Yttria (mol %) | Sample Thickness (mm) | L* Value (dark background) |
|---|---|---|---|
| 42 | 3 | 1.82 | 80.2 |
| 43 | 3 | 1.5 | 78.6 |
| 44 | 3 | 1.26 | 77.7 |
| 45 | 3 | 0.38 | 72.9 |

TABLE 13-continued

Perceptual Lightness (L*) of Yttria-Stabilized Zirconia Samples.

| Ex. # | Yttria (mol %) | Sample Thickness (mm) | L* Value (dark background) |
|---|---|---|---|
| 46 | 5.8 | 2.9 | 73.1 |
| 47 | 5.8 | 2.5 | 73.5 |
| 48 | 5.8 | 2.0 | 72.4 |
| 49 | 5.8 | 1.5 | 71.3 |
| 50 | 5.8 | 1.4 | 70.1 |
| 51 | 5.8 | 0.95 | 67.6 |
| 52 | 5.8 | 0.7 | 66.9 |
| 53 | 5.8 | 0.38 | 63.6 |

Comparison of perceptual lightness (L*) values against sample thickness for the zirconia samples having the tested levels of yttria-stabilization revealed the following strong linear relationships between L* values and sample thickness.

For 3Y samples: $L^* = 5.10 \times (\text{thickness mm}) + 71.01 \ (R^2 = 1.00)$ For 5.8Y samples: $L^* = 5.37 \times (\text{thickness mm}) + 62.44 \ (R^2 = 0.95)$ Dental laboratory and clinical experience using crowns manufactured using unshaded 3Y zirconia has shown that a crown manufactured from the 3Y zirconia and having a wall thickness of 0.8 mm provide an acceptable level of maskability, thereby preventing an undesired level of visibility of a support structure through the sintered crown. Using the formula above, the 0.8 mm thickness for a 3Y zirconia sample corresponds to an L* value of approximately 75, which may be considered a threshold perceptual lightness (L*) value to provide an acceptable level of maskability. As the data in Table 13 shows, the 5.8Y samples having the maximum reported thickness of 2.9 mm only provide an L* value of 73.1, which does not meet the threshold value of 75 to provide the acceptable level of maskability.

Examples 54 Through 77 and Comparative Examples CE1 Through CE4

Yttria-stabilized zirconia crowns were prepared to determine the performance of several masking agents, including determining perceptual lightness values (L*) provided by use of the masking agents on crowns having different yttria mol % concentrations and determining the transition of perceptual lightness values (L*) provided by the masking agents from the body region of the crown to the incisal region.

Bisque yttria-stabilized zirconia anterior crowns comprised of 4.7 mol % yttria and 5.8 mol % yttria were prepared. The sample crowns were treated with masking mixtures prepared as follows. Masking mixtures were prepared by mixing water and the concentrations of masking agents aluminum chloride hexahydrate (AlCl$_3$·6H$_2$O) (commercially available through Alfa Aesar) and zinc sulfate heptahydrate (ZnSO$_4$·7H$_2$O) (commercially available through Sigma Aldrich), as specified in Tables 14 and 15. Liquid masking mixtures were applied to the sample crowns by brush application (painting) using three coats to the internal side surface 203 and top two thirds 205, 206 of the facial surface of the crown (see FIG. 2).

In addition, comparative example crowns were treated with Chang's White Plus coloring liquid (IDS CAD, Centreville VA) according to the manufacturer's recommendations. Coloring liquid was applied to the sample crowns by brush application (painting) using three coats to the internal side surface 203 and top two thirds 205, 206 of the facial surface of the crown (see FIG. 2), as specified in Tables 16 and 17.

The sample crowns and comparative example crowns were then sintered according to the methods provided in Table 3, and prepared for spectral image data analysis according to the test methods provided herein. L* value measurements against a dark background at areas D, A, E, and G are reported in Tables 14-17. The reported "Slope Value from D to G" corresponds to a calculation of the slope of a linear regression line through a plot of the L* values vs. the respective locations of the areas D, A, E, and G, as calculated using the "slope" function on a Microsoft Excel® spreadsheet.

TABLE 14

Perceptual Lightness (L*) Values of 4.7Y Yttria-Stabilized Zirconia Crowns Treated With Inventive Masking Solutions.

| Ex. # | Zn Wt % | Al Wt % | L* at Area D | L* at Area A | L* at Area E | L* at Area G | Slope Value From D to G |
|---|---|---|---|---|---|---|---|
| Control | 0 | 0 | 80 | 82 | 81 | 73 | 10.0 |
| 54 | 50 | 0 | 87 | 86 | 85 | 73 | 21.0 |
| 55 | 10 | 40 | 85 | 86 | 84 | 73 | 19.3 |
| 56 | 20 | 30 | 86 | 86 | 85 | 73 | 18.6 |
| 57 | 25 | 25 | 86 | 86 | 85 | 74 | 18.1 |
| 58 | 30 | 20 | 85 | 85 | 84 | 73 | 18.1 |
| 59 | 40 | 10 | 84 | 84 | 82 | 74 | 15.3 |
| 60 | 0 | 50 | 85 | 87 | 85 | 74 | 17.4 |
| 61 | 9.9 | 0.4 | 80 | 82 | 80 | 74 | 10.3 |
| 62 | 9.9 | 0 | 80 | 82 | 81 | 75 | 8.1 |
| 63 | 0 | 0.4 | 81 | 82 | 80 | 74 | 9.3 |
| 64 | 19.8 | 9.9 | 83 | 83 | 82 | 74 | 12.9 |
| 65 | 39.6 | 19.8 | 85 | 86 | 84 | 75 | 15.9 |

TABLE 15

Perceptual Lightness (L*) Values of 5.8Y Yttria-Stabilized Zirconia Crowns Treated With Inventive Masking Solutions.

| Ex. # | Zn Wt % | Al Wt % | L* at Area D | L* at Area A | L* at Area E | L* at Area G | Slope Value From D to G |
|---|---|---|---|---|---|---|---|
| Control | 0 | 0 | 73 | 73 | 73 | 69 | 5.5 |
| 66 | 50 | 0 | 89 | 90 | 88 | 77 | 19.2 |
| 67 | 10 | 40 | 85 | 86 | 84 | 72 | 20.5 |
| 68 | 20 | 30 | 84 | 85 | 83 | 71 | 19.1 |
| 69 | 25 | 25 | 85 | 86 | 83 | 72 | 21.2 |
| 70 | 30 | 20 | 86 | 86 | 84 | 73 | 19.4 |
| 71 | 40 | 10 | 85 | 87 | 85 | 74 | 16.8 |
| 72 | 0 | 50 | 85 | 85 | 82 | 71 | 22.2 |
| 73 | 9.9 | 0.4 | 80 | 81 | 79 | 72 | 11.1 |
| 74 | 9.9 | 0 | 78 | 79 | 78 | 71 | 9.8 |
| 75 | 0 | 0.4 | 75 | 76 | 75 | 71 | 6.1 |
| 76 | 19.8 | 9.9 | 85 | 86 | 84 | 74 | 16.7 |
| 77 | 39.6 | 19.8 | 86 | 86 | 84 | 72 | 19.9 |

TABLE 16

Perceptual Lightness (L*) Values of 4.7Y Yttria-Stabilized Zirconia Crowns Treated With Chang's White Plus Coloring Liquid.

| Ex. # | L* at Area D | L* at Area A | L* at Area E | L* at Area G | Slope Value From D to G |
|---|---|---|---|---|---|
| Control | 80 | 82 | 80 | 73 | 10.7 |
| CE1 | 94 | 94 | 92 | 72 | 31.7 |
| CE2 | 92 | 91 | 90 | 72 | 30.4 |

TABLE 17

Perceptual Lightness (L*) Values of 5.8Y Yttria-Stabilized Zirconia Crowns Treated With Chang's White Plus Coloring Liquid.

| Ex. # | L* at Area D | L* at Area A | L* at Area E | L* at Area G | Slope Value From D to G |
|---|---|---|---|---|---|
| Control | 73 | 73 | 73 | 69 | 5.5 |
| CE3 | 94 | 94 | 93 | 71 | 33.8 |
| CE4 | 94 | 94 | 93 | 71 | 34.9 |

Figure 10:
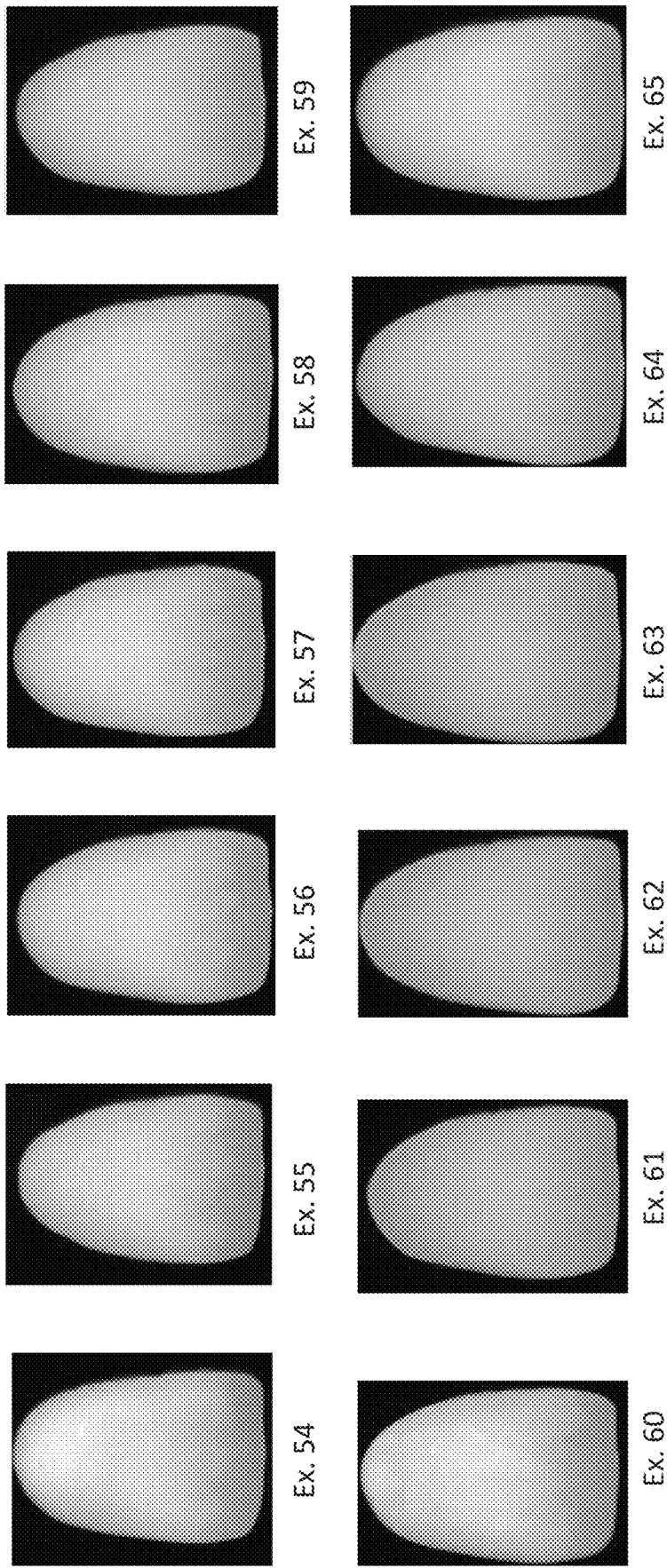
FIG. 10 includes spectral images of crowns corresponding to Examples 54 through 65 described herein.

The spectral images created using the SpectroShade® Micro II device for example 54 through example 65 are shown in FIG. 10. The spectral images created using the SpectroShade® Micro II device for example 54 through example 65 are shown in FIG. 11. The spectral images created using the SpectroShade® Micro II device for comparative examples CE2 and CE3 are shown in FIG. 12. It is apparent from a comparison of the examples and comparative examples shown in FIGS. 10-12 that the large Slope Values produced by the comparative examples correspond to a lightness (L*) and translucency (% T) transition from the body region of the crown to the incisal region that is cosmetically unacceptable. The comparative examples (FIG. 12) produce an abrupt, visible transition in the lightness (L*) and translucency (% T) properties between the main body region and the incisal region of the crown. By comparison, the examples (FIGS. 10-11) produce a natural, gradual transition in the lightness (L*) and translucency (% T) properties between the main body region and the incisal region of the crown.

Preferred transition properties for finished crowns that were treated with the masking solutions described herein were determined to be characterized by having a Measured Lightness Slope Value that followed certain criteria. As used herein, the term "Measured Lightness Slope Value" (MLSV) refers to the slope value (i.e., slope function using the Microsoft Excel® software) of the L* value measurements from Areas D, A, E, and G of a crown, as measured using the SpectroShade® Micro II device and as described herein. In some embodiments, crowns produced using high translucency yttria-stabilized zirconia ceramic materials and treated using the masking solutions and methods described herein provide a Measured Lightness Slope Value (MLSV) of less than 25, such as less than 22, such as less than 20, such as less than 17, such as less than 12. In some embodiments, crowns produced using high translucency yttria-stabilized zirconia ceramic materials and treated using the masking solutions and methods described herein provide a Measured Lightness Slope Value (MLSV) of between 5 and 25, such as between 7 and 22, such as between 8 and 20, such as between 9 and 17, such as between 10 and 12. In still other embodiments, the foregoing crowns also provide perceptual lightness values (L* values) of at least 75 at the Area D location, such as at least 77 at the Area D location, such as at least 79 at the Area D location, such as at least 81 at the Area D location.

We claim:

1. A fully sintered yttria-stabilized zirconia dental restoration comprising:
    a. a sintered zirconia dental restoration comprising zirconia stabilized with 3 mol % yttria to 8 mol % yttria, comprising
        i. an internal surface, and
        ii. a facial surface comprising an overlying region opposite the internal surface, a gingival margin, and an incisal region adjacent an incisal edge; and
    b. a masking agent selected from Zn, Ti, Al, La, Mg, Sc, Si, Sr, Ca, or a combination thereof;
wherein the dental restoration has a perceptual lightness (L*) value of at least 75 at a location that is on a centerline of the facial surface and that is 69% of a distance from the incisal edge toward the gingival margin, and wherein perceptual lightness is measured using a SpectroShade® Micro II spectrophotometer.

2. The dental restoration of claim 1, wherein the masking agent comprises one or more of Zn or Al.

3. The dental restoration of claim 1, wherein the dental restoration comprises a veneer, a crown, a bridge, an implant-supported partial denture, or an implant-supported full-arch denture.

4. The dental restoration of claim 1, wherein the dental restoration has a Measured Lightness Slope Value (MLSV) that is between 7 and 22.

5. The dental restoration of claim 1, wherein the dental restoration has a Measured Lightness Slope Value (MLSV) that is between 9 and 17.

6. The dental restoration of claim 1, wherein a concentration of the masking agent in the overlying region is greater than a concentration of the masking agent in the incisal region, wherein masking agent concentration is measured via energy dispersive spectroscopy (EDS).

7. The dental restoration of claim 1, wherein a concentration of the masking agent in the overlying region is greater than or equal to a concentration of the masking agent in the internal surface, wherein masking agent concentration is measured via energy dispersive spectroscopy (EDS).

* * * * *